(12) United States Patent
Shimamura et al.

(10) Patent No.: US 11,932,798 B2
(45) Date of Patent: Mar. 19, 2024

(54) POLYMERIZABLE LIQUID CRYSTAL COMPOUND, POLYMERIZABLE LIQUID CRYSTAL COMPOSITION, OPTICALLY ANISOTROPIC FILM, OPTICAL FILM, POLARIZING PLATE, AND IMAGE DISPLAY DEVICE

(71) Applicant: FUJIFILM Corporation, Tokyo (JP)

(72) Inventors: Satoshi Shimamura, Kanagawa (JP); Daisuke Hayashi, Kanagawa (JP); Keita Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 471 days.

(21) Appl. No.: 16/732,739

(22) Filed: Jan. 2, 2020

(65) Prior Publication Data

US 2020/0140758 A1    May 7, 2020

Related U.S. Application Data

(63) Continuation of application No. PCT/JP2018/027157, filed on Jul. 19, 2018.

(30) Foreign Application Priority Data

Jul. 19, 2017  (JP) .................................. 2017-140047
Feb. 14, 2018  (JP) .................................. 2018-023937

(51) Int. Cl.
*C09K 19/38*    (2006.01)
*C07C 69/753*    (2006.01)
(Continued)

(52) U.S. Cl.
CPC ........ *C09K 19/3861* (2013.01); *C07C 69/753* (2013.01); *C07D 339/06* (2013.01);
(Continued)

(58) Field of Classification Search
CPC ............ C09K 19/3861; C09K 19/3491; C09K 19/3068; C09K 19/542; C09K 19/3852;
(Continued)

(56) References Cited

U.S. PATENT DOCUMENTS

| 10,173,992 B2 | 1/2019 | Sakamoto et al. |
| 2009/0189120 A1 | 7/2009 | Takeuchi |

(Continued)

FOREIGN PATENT DOCUMENTS

| JP | 2008-273925 A | 11/2008 |
| JP | 2009-179563 A | 8/2009 |

(Continued)

OTHER PUBLICATIONS

International Search Report issued in PCT/JP2018/027157 dated Oct. 9, 2018.

(Continued)

*Primary Examiner* — Ruiyun Zhang
(74) *Attorney, Agent, or Firm* — Edwards Neils LLC; Jean C. Edwards, Esq

(57) ABSTRACT

The present invention has an object to provide a polymerizable liquid crystal compound used for formation of an optically anisotropic film having excellent reciprocal wavelength dispersion and moisture-heat resistance, a polymerizable liquid crystal composition, an optically anisotropic film, an optical film, a polarizing plate, and an image display device. The polymerizable liquid crystal compound of the present invention is a polymerizable liquid crystal compound represented by Formula (1), in which a Clog P value of a group represented by Ar in Formula (1) is 4.3 or more and less than 7.0.

(Continued)

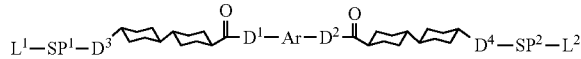

(1)

16 Claims, 1 Drawing Sheet

(51) Int. Cl.
*C07D 339/06* (2006.01)
*C07D 417/04* (2006.01)
*C08F 20/38* (2006.01)
*C09K 19/34* (2006.01)
*C09K 19/56* (2006.01)
*G02B 5/30* (2006.01)
*C09K 19/04* (2006.01)

(52) U.S. Cl.
CPC ............ *C07D 417/04* (2013.01); *C08F 20/38* (2013.01); *C09K 19/3491* (2013.01); *C09K 19/3497* (2013.01); *C09K 19/56* (2013.01); *G02B 5/3016* (2013.01); *C08F 2800/20* (2013.01); *C09K 2019/0448* (2013.01); *C09K 2323/03* (2020.08); *C09K 2323/031* (2020.08); *C09K 2323/035* (2020.08); *G02B 5/3083* (2013.01)

(58) Field of Classification Search
CPC ............ C09K 19/54; C09K 2019/0448; C09K 2323/03; C09K 2323/031; C09K 2323/035; G02F 1/133528; G02F 1/13363; C07D 339/06; G02B 5/3016
USPC ................... 428/1.3, 1.31, 1.33; 349/96, 117
See application file for complete search history.

(56) References Cited

U.S. PATENT DOCUMENTS

| | | |
|---|---|---|
| 2009/0268143 A1 | 10/2009 | Takeuchi et al. |
| 2010/0045901 A1 | 2/2010 | Jehira et al. |
| 2017/0329063 A1 | 11/2017 | Sakai et al. |
| 2017/0369783 A1 | 12/2017 | Horiguchi et al. |
| 2018/0201701 A1* | 7/2018 | Muramatsu .......... G02B 5/3041 |
| 2018/0327668 A1 | 11/2018 | Horiguchi et al. |
| 2018/0348417 A1 | 12/2018 | Shiraiwa et al. |
| 2019/0352567 A1 | 11/2019 | Hayashi et al. |
| 2021/0284766 A1* | 9/2021 | Endo ...................... G02F 1/1335 |

FOREIGN PATENT DOCUMENTS

| | | | |
|---|---|---|---|
| JP | 2009-242717 A | 10/2009 | |
| JP | 2009-265317 A | 11/2009 | |
| JP | 2010-031223 A | 2/2010 | |
| JP | 2010084032 A * | 4/2010 | |
| JP | 2016-081035 A | 5/2016 | |
| JP | 2018-025770 A | 2/2018 | |
| WO | 2014/010325 A1 | 1/2014 | |
| WO | 2016/104317 A1 | 6/2016 | |
| WO | 2016/125839 A1 | 8/2016 | |
| WO | 2017/038267 A1 | 3/2017 | |
| WO | 2017/043438 A1 | 3/2017 | |
| WO | WO-2017057545 A1 * | 4/2017 | .......... G02B 5/3091 |
| WO | 2017/150613 A1 | 9/2017 | |
| WO | WO-2018012390 A1 * | 1/2018 | .............. C08F 22/24 |
| WO | 2018/155498 A1 | 8/2018 | |

OTHER PUBLICATIONS

Written Opinion issued in PCT/JP2018/027157 dated Oct. 9, 2018.
International Preliminary Report on Patentability completed by WIPO dated Jan. 21, 2020 in connection with International Patent Application No. PCT/JP2018/027157.
Office Action, issued by the Korean Intellectual Property Office dated Jan. 12, 2021, in connection with Korean Patent Application No. 10-2019-7038897.
Office Action, issued by the Japanese Patent Office dated Mar. 30, 2021, in connection with Japanese Patent Application No. 2019-530599.
Office Action, issued by the State Intellectual Property Office dated Mar. 30, 2022, in connection with corresponding Chinese Patent Application No. 201880047714.4.
Office Action, issued by the Japanese Patent Office dated Oct. 27, 2020, in connection with Japanese Patent Application No. 2019-530599.
Office Action, issued by the State Intellectual Property Office dated Sep. 5, 2022, in connection with corresponding Chinese Patent Application No. 201880047714.4.

* cited by examiner

POLYMERIZABLE LIQUID CRYSTAL COMPOUND, POLYMERIZABLE LIQUID CRYSTAL COMPOSITION, OPTICALLY ANISOTROPIC FILM, OPTICAL FILM, POLARIZING PLATE, AND IMAGE DISPLAY DEVICE

CROSS-REFERENCE TO RELATED APPLICATIONS

This application is a Continuation of PCT International Application No. PCT/JP2018/027157 filed on Jul. 19, 2018, which was published under PCT Article 21(2) in Japanese, and which claims priority under 35 U.S.C. § 119(a) to Japanese Patent Application No. 2017-140047 filed on Jul. 19, 2017 and Japanese Patent Application No. 2018-023937 filed on Feb. 14, 2018. The above applications are hereby expressly incorporated by reference, in their entirety, into the present application.

BACKGROUND OF THE INVENTION

1. Field of the Invention

The present invention relates to a polymerizable liquid crystal compound, a polymerizable liquid crystal composition, an optically anisotropic film, an optical film, a polarizing plate, and an image display device.

2. Description of the Related Art

A polymerizable compound exhibiting reciprocal wavelength dispersion enables, for example, conversion of accurate light ray wavelengths over a wide wavelength range and reduction in the thickness of a phase difference film due to its high refractive index, and therefore, the polymerizable compound has been actively studied.

Furthermore, for a polymerizable compound exhibiting reciprocal wavelength dispersion, T-type molecular design guidelines have generally been applied and it has been required to decrease the wavelength of a major axis of the molecule and increase the wavelength of a minor axis positioned at the center of the molecule.

In this regard, it is known that a cycloalkylene skeleton having no absorption wavelength is used for the connection between a skeleton of the minor axis positioned at the center of the molecule (hereinafter also referred to as a "reciprocal wavelength dispersion expressing portion") and the major axis of the molecule (see, for example, JP2008-273925A, JP2010-031223A, WO2014/010325A, and JP2016-081035A).

SUMMARY OF THE INVENTION

The present inventors have conducted studies on JP2008-273925A, JP2010-031223A, WO2014/010325A, and JP2016-081035A, and have thus found that the reciprocal wavelength dispersion of an optically anisotropic film formed is deteriorated in some cases, depending on polymerization conditions such as the type of the polymerizable compound, the type of a polymerization initiator, and a curing temperature, and that there is a problem that the birefringence index of an optically anisotropic film formed changes in a case where the optically anisotropic film is exposed to a high temperature and a high humidity, that is, the moisture-heat resistance of an optically anisotropic film formed is deteriorated in some cases.

Therefore, an object of the present invention is to provide a polymerizable liquid crystal compound used for formation of an optically anisotropic film having excellent reciprocal wavelength dispersion and moisture-heat resistance, a polymerizable liquid crystal composition, an optically anisotropic film, an optical film, a polarizing plate, and an image display device.

The present inventors have conducted extensive studies to accomplish the object, and as a result, have found that by allowing an aromatic ring constituting a reciprocal wavelength dispersion expressing portion to satisfy a predetermined Clog P value, and incorporating a predetermined skeleton in the major axis direction of a molecule having the reciprocal wavelength dispersion expressing portion at the center, both the reciprocal wavelength dispersion and the moisture-heat resistance of an optically anisotropic film formed are improved, thereby completing the present invention.

That is, the present inventors have found that the object can be accomplished by the following configurations.

[1] A polymerizable liquid crystal compound represented by Formula (1) which will be described later,
in which a Clog P value of a group represented by Ar in Formula (1) which will be described later is 4.3 or more and less than 7.0.

[2] The polymerizable liquid crystal compound as described in [1],
in which Ar in Formula (1) is an aromatic ring which will be described later consisting of the group represented by Formula (Ar-2) which will be described later, and $Z^1$ in Formula (Ar-2) which will be described later represents a monovalent aliphatic hydrocarbon group having 3 to 20 carbon atoms, a monovalent aromatic hydrocarbon group having 6 to 20 carbon atoms, a halogen atom, $-OR^6$, $-NR^7R^8$, or $-SR^9$.

[3] The polymerizable liquid crystal compound as described in [1],
in Ar in Formula (1) which will be described later is any aromatic ring selected from the group consisting of groups represented by Formulae (Ar-1), (Ar-4), and (Ar-5) which will be described later, and $Z^1$ and $Z^2$ in Formulae (Ar-1), (Ar-4), and (Ar-5) which will be described later each represent a hydrogen atom.

[4] The polymerizable liquid crystal compound as described in any one of [1] to [3], in which $D^1$ and $D^2$ in Formula (1) which will be described later each represent $-O-$, and $D^3$ and $D^4$ in Formula (1) which will be described later each represent $-O-CO-$.

[5] A polymerizable liquid crystal composition comprising the polymerizable liquid crystal compound as described in any one of [1] to [4].

[6] The polymerizable liquid crystal composition as described in [5], further comprising a polymerizable compound having one or more polymerizable groups, which is different from the polymerizable liquid crystal compound.

[7] An optically anisotropic film obtained by polymerization of the polymerizable liquid crystal composition as described in [5] or [6].

[8] An optical film comprising the optically anisotropic film as described in [7].

[9] A polarizing plate comprising:
the optical film as described in [8]; and
a polarizer.

[10] An image display device comprising:
the optical film as described in [8] or the polarizing plate as described in [9].

According to the present invention, it is possible to provide a polymerizable liquid crystal compound used for formation of an optically anisotropic film having excellent reciprocal wavelength dispersion and moisture-heat resistance, a polymerizable liquid crystal composition, an optically anisotropic film, an optical film, a polarizing plate, and an image display device.

DESCRIPTION OF THE PREFERRED EMBODIMENTS

Figure 1A:
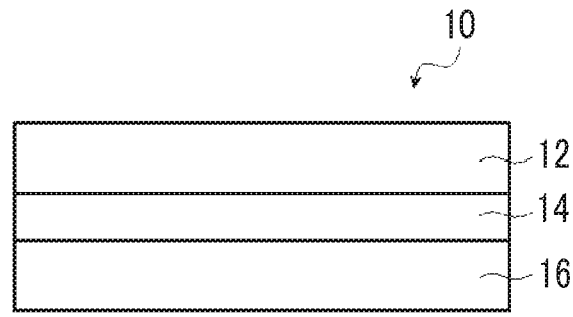
FIG. 1A is a schematic cross-sectional view showing an example of an optical film of an embodiment of the present invention.

Hereinafter, the present invention will be described in detail.

Descriptions on the constitutional requirements which will be described below are made based on representative embodiments of the present invention in some cases, but it should not be construed that the present invention is limited to such embodiments.

Furthermore, in the present specification, a numerical range expressed using "to" means a range that includes the preceding and succeeding numerical values of "to" as the lower limit value and the upper limit value, respectively.

In addition, in the present specification, the bonding direction of a divalent group (for example, —O—CO—) as presented is not particularly limited, and for example, in a case where $D^3$ in Formula (1) which will be described later is —O—CO—, $D^3$ may be either *1-O—CO-*2 or *1-CO—O-*2, in which *1 represents a bonding position to the $SP^1$ side and *2 represents a bonding position to the cyclohexane ring side.

[Polymerizable Liquid Crystal Compound]

A polymerizable liquid crystal compound of an embodiment of the present invention is a compound represented by Formula (1).

Furthermore, in the polymerizable liquid crystal compound of the embodiment of the present invention, the Clog P value of a group represented by Ar in Formula (1) is 4.3 or more and less than 7.0.

Here, the Clog P value is a value determined by calculation of a common logarithm log P of a partition coefficient P between 1-octanol and water. With regard to a method or software used for calculation of the Clog P value, a known method or software can be used, but in the present invention, a Clog P program incorporated into ChemBioDraw Ultra 13.0 from Cambridge Soft is used unless otherwise specified. Furthermore, in the present invention, the Clog P value is a value obtained by rounding down to two decimal points, for example, the number "4.29" is not within the range of 4.3 or more and less than 7.0 and the number "6.98" is within the range of 4.3 or more and less than 7.0.

In the present invention, by setting the Clog P value of the group (aromatic ring) represented by Ar in Formula (1) to 4.3 or more and less than 7.0 and incorporating a skeleton in which cyclohexane rings are linked to each other via a single bond in the major axis direction of a molecule having Ar at the center as described above, the reciprocal wavelength dispersion and the moisture-heat resistance of an optically anisotropic film formed is improved.

A reason therefor is not specifically clear, but is presumed to be as follows by the present inventors.

That is, it is considered that by allowing the compound represented by Formula (1) to have a structure in which cyclohexane rings are linked to each other via a single bond in the major axis direction of the molecule and not to have a benzene ring in the major axis direction of the molecule, a shorter wavelength can be attained, and as a result, the reciprocal wavelength dispersion of the optically anisotropic film formed is improved.

In addition, it is considered that in the compound represented by Formula (1), when the aromatic ring constituting the reciprocal wavelength dispersion expressing portion has a Clog P value of within the range of 4.3 or more and less than 7.0, hydrophobicity of the reciprocal wavelength dispersion expressing portion and the moisture-heat resistance are improved.

Hereinafter, with regard to the polymerizable liquid crystal compound of the embodiment of the present invention, the configuration of Formula (1) will be described in detail.

The polymerizable liquid crystal compound of the embodiment of the present invention is a polymerizable liquid crystal compound represented by Formula (1), as described above.

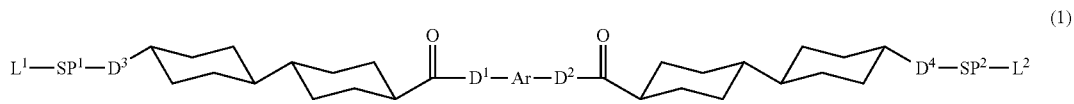

(1)

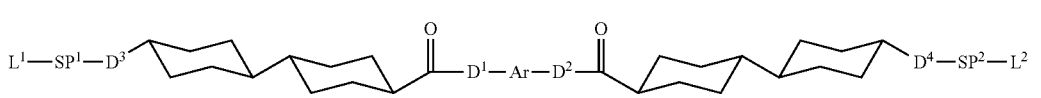

(1)

In Formula (1), $D^1$ and $D^2$ each independently represent —O—, —S—, or —$NR^1$—, and $D^3$ and $D^4$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—, $R^1$, $R^2$, $R^3$, and $R^4$ each independently represent a hydrogen atom, a fluorine atom, or an alkyl group having 1 to 4 carbon atoms. Incidentally, in Formula (1), $SP^1$ and $SP^2$ each independently represent a single bond, a linear or branched alkylene group having 1 to 12 carbon atoms, or a divalent linking group in which one or more of —$CH_2$—'s constituting the linear or branched alkylene group having 1 to 12 carbon atoms are substituted with —O—, —S—, —NH—, —N(Q)-, or —CO—, and Q represents a substituent.

Furthermore, in Formula (1), $L^1$ and $L^2$ each independently represent a monovalent organic group, and at least one of $L^1$ or $L^2$ represents a polymerizable group. It should be noted that in a case where Ar is an aromatic ring represented by Formula (Ar-3) which will be described later, at least one of $L^1$ or $L^2$, or $L^3$ or $L^4$ in Formula (Ar-3) which will be described later represents a polymerizable group.

In addition, in Formula (1), Ar represents any one aromatic ring selected from the group consisting of groups represented by Formulae (Ar-1) to (Ar-5) which will be described later.

Suitable examples of the linear or branched alkylene group having 1 to 12 carbon atoms represented by each of $SP^1$ and $SP^2$ in Formula (1) include a methylene group, an ethylene group, a propylene group, a butylene group, a pentylene group, a hexylene group, a methylhexylene group, and a heptylene group.

Moreover, examples of the monovalent organic group represented by each of $L^1$ and $L^2$ in Formula (1) include an alkyl group, an aryl group, and a heteroaryl group. The alkyl group may be linear, branched, or cyclic, but is preferably linear. The number of carbon atoms of the alkyl group is preferably 1 to 30, more preferably 1 to 20, and still more preferably 1 to 10. Further, the aryl group may be a monocycle or a polycycle, but is preferably the monocycle. The number of carbon atoms of the aryl group is preferably 6 to 25, and more preferably 6 to 10. Further, the heteroaryl group may be a monocycle or a polycycle. The number of heteroatoms constituting the heteroaryl group is preferably 1 to 3. The heteroatoms constituting the heteroaryl group is preferably a nitrogen atom, a sulfur atom, or an oxygen atom. The number of carbon atoms of the heteroaryl group is preferably 6 to 18, and more preferably 6 to 12. In addition, the alkyl group, the aryl group, and the heteroaryl group may be unsubstituted or have a substituent. Examples of the substituent include the same ones as the substituents which may be contained in $Y^1$ in Formula (Ar-1) which will be described later.

On the other hand, in Formula (1), the polymerizable group represented by at least one of $L^1$ or $L^2$ is not particularly limited, but is preferably a polymerizable group which is radically polymerizable or cationically polymerizable.

A generally known radically polymerizable group can be used as the radically polymerizable group, and suitable examples thereof include an acryloyl group and a methacryloyl group. In this case, it is known that the acryloyl group generally has a high polymerization rate, and from the viewpoint of improvement of productivity, the acryloyl group is preferable, but the methacryloyl group can also be used in the same manner as the polymerizable group.

A generally known cationically polymerizable group can be used as the cationically polymerizable group, and specific examples thereof include an alicyclic ether group, a cyclic acetal group, a cyclic lactone group, a cyclic thioether group, a spiroorthoester group, and a vinyloxy group. Among those, the alicyclic ether group or the vinyloxy group is preferable, and the epoxy group, the oxetanyl group, or the vinyloxy group is particularly preferable.

Particularly preferred examples of the polymerizable group include the following groups.

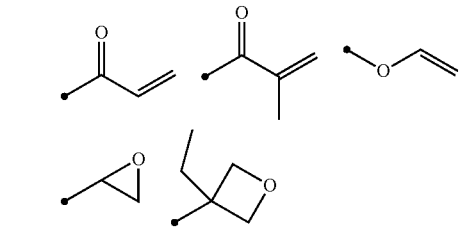

Moreover, in Formula (1), Ar represents any one aromatic ring selected from the group consisting of groups represented by Formulae (Ar-1) to (Ar-5). Further, in Formulae (Ar-1) to (Ar-5), * represents a bonding position to $D^1$ or $D^2$ in Formula (1).

(Ar-1)

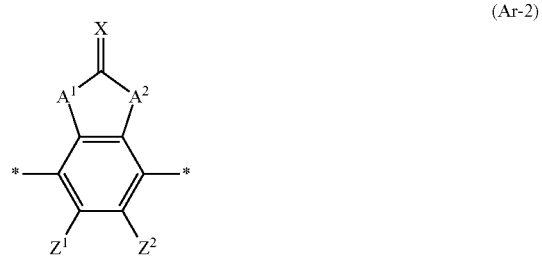

(Ar-2)

-continued

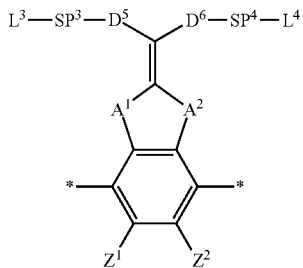

(Ar-3)

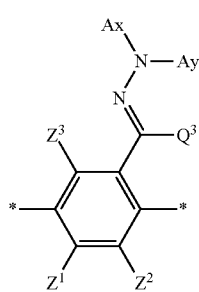

(Ar-4)

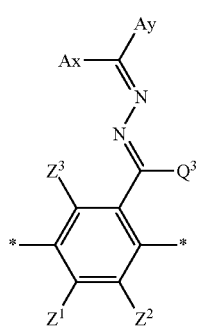

(Ar-5)

Here, in Formula (Ar-L), $Q^1$ represents N or CH, $Q^2$ represents —S—, —O—, or —N($R^5$)—, $R^5$ represents a hydrogen atom or an alkyl group having 1 to 6 carbon atoms, and $Y^1$ represents an aromatic hydrocarbon group having 6 to 12 carbon atoms or an aromatic heterocyclic group having 3 to 12 carbon atoms, each of which may have a substituent.

Specific examples of the alkyl group having 1 to 6 carbon atoms represented by $R^5$ include a methyl group, an ethyl group, a propyl group, an isopropyl group, an n-butyl group, an isobutyl group, a sec-butyl group, a tert-butyl group, an n-pentyl group, and an n-hexyl group.

Examples of the aromatic hydrocarbon group having 6 to 12 carbon atoms represented by $Y^1$ include aryl groups such as a phenyl group, a 2,6-diethylphenyl group, and a naphthyl group.

Examples of the aromatic heterocyclic group having 3 to 12 carbon atoms represented by $Y^1$ include heteroaryl groups such as a thienyl group, a thiazolyl group, a furyl group, and a pyridyl group.

Furthermore, examples of the substituent which may be contained in $Y^1$ include an alkyl group, an alkoxy group, and a halogen atom.

As the alkyl group, for example, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a t-butyl group, and a cyclohexyl group) is more preferable, an alkyl group having 1 to 4 carbon atoms is still more preferable, and the methyl group or the ethyl group is particularly preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, and a methoxy ethoxy group) is more preferable, an alkoxy group having 1 to 4 carbon atoms is still more preferable, and the methoxy group or the ethoxy group is particularly preferable.

Examples of the halogen atom include a fluorine atom, a chlorine atom, a bromine atom, and an iodine atom, and among these, the fluorine atom or the chlorine atom is preferable.

In addition, in Formulae (Ar-1) to (Ar-5), $Z^1$, $Z^2$, and $Z^3$ each independently represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$OR^6$, —$NR^7R^8$, or —$SR^9$, $R^6$ to $R^9$ each independently represent a hydrogen atom or an alkyl group having 1 to 6 carbon atoms, and $Z^1$ and $Z^2$ may be bonded to each other to form an aromatic ring.

As the monovalent aliphatic hydrocarbon group having 1 to 20 carbon atoms, an alkyl group having 1 to 15 carbon atoms is preferable, an alkyl group having 1 to 8 carbon atoms is more preferable, and specifically, a methyl group, an ethyl group, an isopropyl group, a tert-pentyl group (1,1-dimethylpropyl group), a tert-butyl group, or a 1,1-dimethyl-3,3-dimethyl-butyl group is still more preferable, and the methyl group, the ethyl group, or the tert-butyl group is particularly preferable.

Examples of the monovalent alicyclic hydrocarbon group having 3 to 20 carbon atoms include monocyclic saturated hydrocarbon groups such as a cyclopropyl group, a cyclobutyl group, a cyclopentyl group, a cyclohexyl group, a cycloheptyl group, a cyclooctyl group, a cyclodecyl group, a methylcyclohexyl group, and an ethylcyclohexyl group; monocyclic unsaturated hydrocarbon groups such as a cyclobutenyl group, a cyclopentenyl group, a cyclohexenyl group, a cycloheptenyl group, a cyclooctenyl group, a cyclodecenyl group, a cyclopentadienyl group, a cyclohexadienyl group, a cyclooctadienyl group, and a cyclodecadiene; and polycyclic saturated hydrocarbon groups such as a bicyclo[2.2.1]heptyl group, a bicyclo[2.2.2]octyl group, a tricyclo[5.2.1.0$^{2,6}$]decyl group, a tricyclo[3.3.1.1$^{3,7}$]decyl group, a tetracyclo[6.2.1.1$^{3,6}$.0$^{2,7}$]dodecyl group, and an adamantyl group. Specific examples of the monovalent aromatic hydrocarbon group having 6 to 20 carbon atoms include a phenyl group, a 2,6-diethylphenyl group, a naphthyl group, and a biphenyl group, and an aryl group having 6 to 12 carbon atoms (particularly a phenyl group) is preferable.

Examples of the halogen atom include a fluorine atom, a chlorine atom, a bromine atom, and an iodine atom, and among these, the fluorine atom, the chlorine atom, or the bromine atom is preferable.

On the other hand, specific examples of the alkyl group having 1 to 6 carbon atoms represented by each of $R^6$ to $R^8$ include a methyl group, an ethyl group, a propyl group, an isopropyl group, an n-butyl group, an isobutyl group, a sec-butyl group, a tert-butyl group, an n-pentyl group and an n-hexyl group.

In addition, in Formulae (Ar-2) and (Ar-3), $A^1$ and $A^2$ each independently represent a group selected from the group consisting of —O—, —N($R^{10}$)—, —S—, and —CO—, and $R^{10}$ represents a hydrogen atom or a substituent.

Examples of the substituent represented by $R^{10}$ include the same ones as the substituents which may be contained in $Y^1$ in Formula (Ar-1).

Furthermore, in Formula (Ar-2), X represents a hydrogen atom or a non-metal atom of Groups 14 to 16 to which a substituent may be bonded.

Moreover, examples of the non-metal atom of Groups 14 to 16 represented by X include an oxygen atom, a sulfur atom, a nitrogen atom having a substituent, and a carbon atom having a substituent, and specific examples of the substituent include an alkyl group, an alkoxy group, an alkyl-substituted alkoxy group, a cyclic alkyl group, an aryl group (for example, a phenyl group and a naphthyl group), a cyano group, an amino group, a nitro group, an alkylcarbonyl group, a sulfo group, and a hydroxyl group.

In addition, in Formula (Ar-3), $D^1$ and $D^6$ each independently represent a single bond, —CO—O—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—. $R^1$, $R^2$, $R^3$, and $R^4$ each independently represent a hydrogen atom, a fluorine atom, or an alkyl group having 1 to 4 carbon atoms.

Moreover, in Formula (Ar-3), $SP^3$ and $SP^4$ each independently represent a single bond, a linear or branched alkylene group having 1 to 12 carbon atoms, or a divalent linking group in which one or more of —$CH_2$-'s constituting the linear or branched alkylene group having 1 to 12 carbon atoms are substituted with —O—, —S—, —NH—, —N(Q)-, or —CO—, and Q represents a substituent. Examples of the substituent include the same ones as the substituents which may be contained in $Y^1$ in Formula (Ar-1).

Furthermore, in Formula (Ar-3), $L^3$ and $L^4$ each independently represent a monovalent organic group, and at least one of $L^3$ or $L^4$, or $L^1$ or $L^2$ in Formula (1) represents a polymerizable group.

Examples of the monovalent organic group include the same ones as the monovalent organic groups described in $L^1$ and $L^2$ in Formula (1).

In addition, examples of the polymerizable group include the same ones as the polymerizable groups described in $L^1$ and $L^2$ in Formula (1).

Moreover, in Formulae (Ar-4) and (Ar-5), Ax represents an organic group having 2 to 30 carbon atoms, which has at least one aromatic ring selected from the group consisting of an aromatic hydrocarbon ring and an aromatic heterocyclic ring.

Furthermore, in Formulae (Ar-4) and (Ar-5), Ay represents a hydrogen atom, an alkyl group having 1 to 12 carbon atoms, which may have a substituent, or an organic group having 2 to 30 carbon atoms, which has at least one aromatic ring selected from the group consisting of an aromatic hydrocarbon ring and an aromatic heterocyclic ring.

Here, the aromatic rings in each of Ax and Ay may have a substituent, and Ax and Ay may be bonded to each other to form a ring.

In addition, $Q^3$ represents a hydrogen atom or an alkyl group having 1 to 6 carbon atoms, which may have a substituent.

Examples of each of Ax and Ay include the ones described in paragraphs 0039 to 0095 of WO2014/010325A.

Incidentally, specific examples of the alkyl group having 1 to 6 carbon atoms represented by $Q^3$ include a methyl group, an ethyl group, a propyl group, an isopropyl group, an n-butyl group, an isobutyl group, a sec-butyl group, a tert-butyl group, an n-pentyl group, and an n-hexyl group, and examples of the substituent include the same ones as the substituents which may be contained in $Y^1$ in Formula (Ar-1).

In the present invention, in a case where Ar in Formula (1) is an aromatic ring consisting of the group represented by Formula (Ar-2), for a reason that moisture-heat resistance of an optically anisotropic film formed is further improved, a compound in which $Z^1$ in Formula (Ar-2) represents a monovalent aliphatic hydrocarbon group having 3 to 20 carbon atoms, a monovalent aromatic hydrocarbon group having 6 to 20 carbon atoms, a halogen atom, —OR6, —$NR^7R^8$, or —$SR^9$ is preferable.

In the present invention, in a case where Ar in Formula (1) is any aromatic ring selected from the group consisting of the groups represented by Formulae (Ar-1), (Ar-4), and (Ar-5), Ar in Formula (1) is preferably a compound in which both $Z^1$ and $Z^2$ in Formulae (Ar-1), (Ar-4), and (Ar-5) represents a hydrogen atom from the viewpoint of liquid crystallinity.

In the present invention, as the polymerizable compound represented by Formula (1), a compound in which $D^1$ and $D^2$ each represent —O—, and $D^3$ and $D^4$ each represent —O—CO— is preferable for a reason that the compound is easily synthesized.

In the present invention, specific examples of the polymerizable compound represented by Formula (1) include compounds represented by Formulae (I) to (V), and specifically the compounds of Formulae (I) to (V), which have side chain structures shown in Tables 1 and 2 as K (side chain structure).

Furthermore, in Tables 1 and 2 below, "*" shown in the side chain structure of K represents a bonding position to an aromatic ring.

Incidentally, in the following description, a compound represented by Formula (I) and having a group shown in 1-1 in Table 1 below is presented as "Compound (I-1-1)", and compounds having other structural formulae and groups are also presented in the same manner. For example, a compound represented by Formula (II) and having a group shown in 2-3 in Table 2 below is denoted as "Compound (II-2-3)".

In addition, in the side chain structures shown in 1-2 in Table 1 below and 2-2 in Table 2 below, a group adjacent to each of the acryloyloxy group and the methacryloyl group represents a propylene group (a group in which a methyl group is substituted with an ethylene group), and represents a mixture of position isomers in which the positions of the methyl group are different.

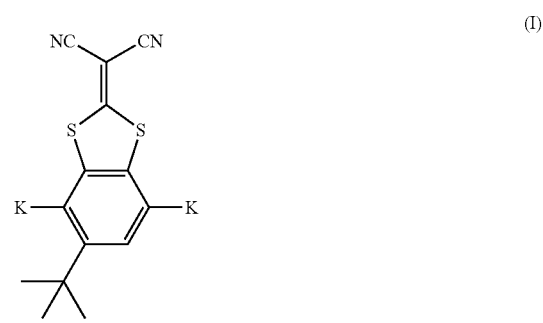

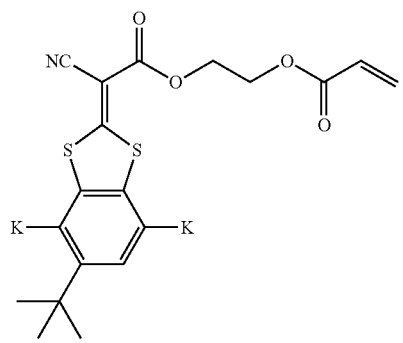
(II)
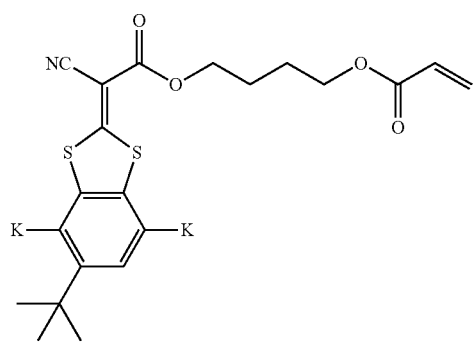
(III)
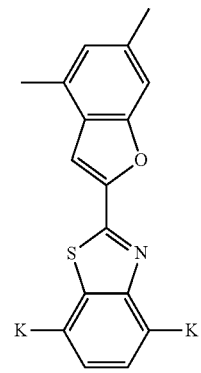
(IV)
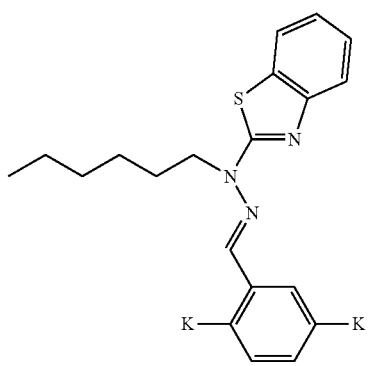
(V)
TABLE 1
| | K (side chain structure) |
|---|---|
| 1-1 | ![structure] |
| 1-2 | ![structure] |
| 1-3 | ![structure] |
| 1-4 | ![structure] |
| 1-5 | ![structure] |

TABLE 1-continued

| | K (side chain structure) |
|---|---|
| 1-6 | |
| 1-7 | |
| 1-8 | |
| 1-9 | |
| 1-10 | |
| 1-11 | |
| 1-12 | |
| 1-13 | |

TABLE 2

| | K (side chain structure) |
|---|---|
| 2-1 | |
| 2-2 | |

TABLE 2-continued
| K (side chain structure) |
2-3 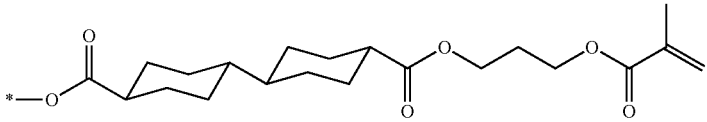 [SMILES: *OC(=O)C1CCC(C2CCC(C(=O)OCCCOC(=O)C(=C)C)CC2)CC1]
2-4 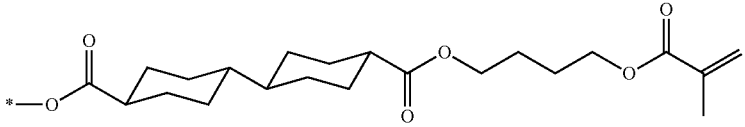 [SMILES: *OC(=O)C1CCC(C2CCC(C(=O)OCCCCOC(=O)C(=C)C)CC2)CC1]
2-5 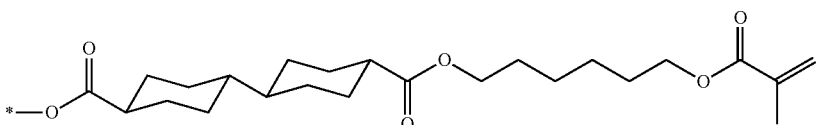
2-6 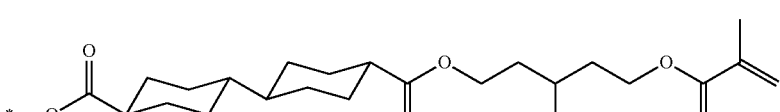
2-7 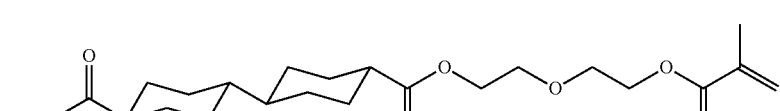
2-8 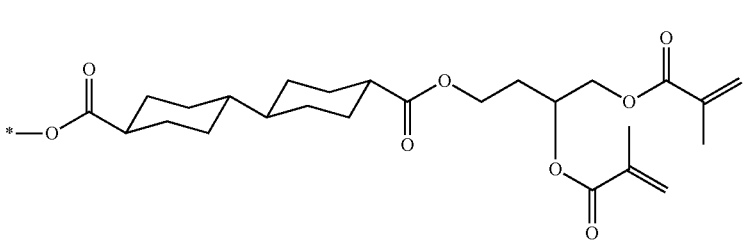 [SMILES: *OC(=O)C1CCC(C2CCC(C(=O)OCCC(COC(=O)C(=C)C)OC(=O)C(=C)C)CC2)CC1]
2-9 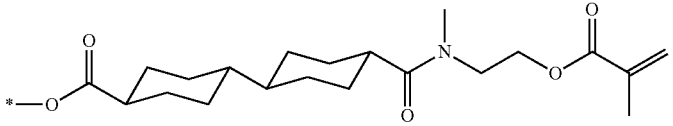 [SMILES: *OC(=O)C1CCC(C2CCC(C(=O)N(C)CCOC(=O)C(=C)C)CC2)CC1]
2-10 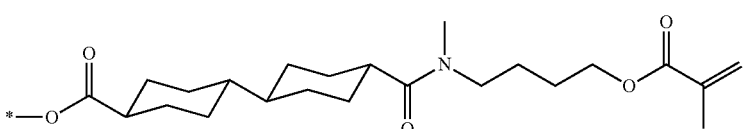
2-11 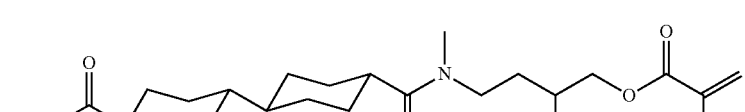
2-12 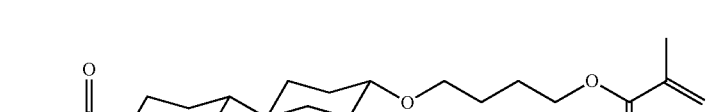

TABLE 2-continued

K (side chain structure)

2-13

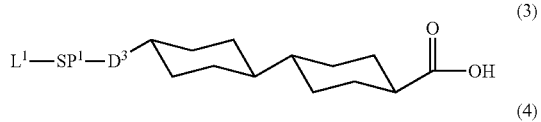

In the present invention, for a reason that the moisture-heat resistance of the optically anisotropic film formed is further improved, the Clog P value of the group represented by Ar in Formula (1) is preferably 4.4 or more and 6.9 or less.

[Method for Synthesizing Polymerizable Liquid Crystal Compound]

A method for synthesizing the polymerizable liquid crystal compound of the embodiment of the present invention is not particularly limited, but examples thereof include a method including:

a first esterification step of reacting a compound represented by Formula (2) with a compound represented by Formula (3) to produce a phenol compound; and a second esterification step of reacting the phenol reactant obtained in the first esterification step with a compound represented by Formula (4) to obtain the polymerizable liquid crystal compound of the embodiment of the present invention.

Moreover, in a case where the compound represented by Formula (3) and the compound represented by Formula (4) are the same as each other, it is possible to synthesize the polymerizable liquid crystal compound of the embodiment of the present invention by reacting the compound represented by Formula (2) with the compound represented by Formula (3).

Furthermore, it is possible to obtain a mixture of a plurality of polymerizable liquid crystal compounds having different structures of the terminals by mixing the compound represented by Formula (2), the compound represented by Formula (3), and the compound represented by Formula (4) to perform a reaction.

In addition, two or more kinds of the compounds represented by Formula (2) may be used in combination, and in a case where the two or more kinds of the compounds represented by Formula (2) are used in combination, the polymerizable liquid crystal compound of the embodiment of the present invention can be obtained as a mixture of a plurality of polymerizable liquid crystal compounds having different structures of Ar corresponding to a reciprocal wavelength dispersion expressing portion.

 (2)

 (3)

(4)

Here, Ar in Formula (2), L, $SP^1$, and $SP^1$ in Formula (3), and $L^2$, $SP^2$, and $D^4$ in Formula (4) are all the same as described in Formula (1).

In addition, the polymerizable liquid crystal compound obtained by the above-mentioned synthesis method is a compound in which $D^1$ and $D^2$ in Formula (1) each represent —O—, and $D^3$ and $D^4$ in Formula (1) each represent —O—CO— among the polymerizable liquid crystal compounds represented by Formula (1).

<Esterification Reaction>

The above-mentioned first esterification step and second esterification step, and the step of reacting the compound represented by Formula (2) and the compound represented by Formula (3) in a case where the compound represented by Formula (3) and the compound represented by Formula (4) are the same as each other are not particularly limited in terms of the reaction conditions, and reaction conditions for esterification known in the related art can be appropriately adopted.

For example, the reaction is preferably performed at a temperature of −10° C. to 40° C., more preferably performed at a temperature of −5° C. to 30° C., and still more preferably performed at a temperature of 0° C. to 20° C.

In addition, the reaction is preferably performed for a reaction time of 10 minutes to 24 hours, more preferably performed for a reaction time of 1 hour to 10 hours, and still more preferably performed for a reaction time of 1 hour to 8 hours.

[Polymerizable Liquid Crystal Composition]

The polymerizable liquid crystal composition of the embodiment of the present invention is a polymerizable liquid crystal composition containing the above-mentioned polymerizable liquid crystal compound of the embodiment of the present invention, and can contain other polymerizable compounds, polymerization initiators, solvents, or the like which will be described later, in addition to the polymerizable liquid crystal compound of the embodiment of the present invention.

[Other Polymerizable Compounds]

The polymerizable liquid crystal composition of the embodiment of the present invention may include other polymerizable compounds having one or more polymerizable groups, in addition to the above-mentioned polymerizable liquid crystal compound of the embodiment of the present invention.

Here, the polymerizable group contained in such other polymerizable compounds is not particularly limited, and examples thereof include a (meth)acryloyl group, a vinyl group, a styryl group, and an allyl group. Among these, the (meth)acryloyl group is preferably contained.

For a reason that the moisture-heat resistance of the optically anisotropic film formed is further improved, such other polymerizable compounds are preferably other polymerizable compounds having 1 to 4 polymerizable groups, and more preferably other polymerizable compounds having 2 polymerizable groups.

Examples of such other polymerizable compounds include the compounds described in paragraphs 0073 and 0074 of JP2016-053709A.

Other examples of such other polymerizable compounds include the compounds represented by Formulae (M1), (M2), and (M3) described in paragraphs 0030 to 0033 of JP2014-077068A, and more specifically, the specific examples described in paragraphs 0046 to 0055 of the same publication.

In addition, as such other polymerizable compounds, the compounds having the structures of Formulae (1) to (3) described in JP2014-198814A can also be preferably used, and more specifically, examples of such other polymerizable compounds include the specific examples described in paragraphs 0020 to 0035, 0042 to 0050, 0056, and 0057 of the same publication.

In addition, examples of such other polymerizable compounds include a compound which is a polymerizable liquid crystal compound represented by Formula (1) and in which the Clog P value of the group represented by Ar in Formula (1) is less than 4.3, and for a reason that the reciprocal wavelength dispersion of the optically anisotropic film formed is further improved, suitable examples thereof include a compound in which the Clog P value of the group represented by Ar in Formula (1) is 3.5 or less.

In a case of containing such other polymerizable compounds, a content thereof is preferably less than 50% by mass, more preferably 40% by mass or less, and still more preferably 10% to 30% by mass, with respect to the total mass of the above-mentioned polymerizable liquid crystal compound of the embodiment of the present invention.

[Polymerization Initiator]

The polymerizable liquid crystal composition of the embodiment of the present invention preferably contains a polymerization initiator.

The polymerization initiator to be used is preferably a photopolymerization initiator capable of initiating a polymerization reaction upon irradiation with ultraviolet rays.

Examples of the photopolymerization initiator include α-carbonyl compounds (described in each of the specifications of U.S. Pat. Nos. 2,367,661A and 2,367,670A), acyloin ethers (described in U.S. Pat. No. 2,448,828A), α-hydrocarbon-substituted aromatic acyloin compounds (described in U.S. Pat. No. 2,722,512A), multinuclear quinone compounds (described in each of the specifications of U.S. Pat. Nos. 3,046,127A and 2,951,758A), combinations of a triarylimidazole dimer and p-aminophenyl ketone (described in U.S. Pat. No. 3,549,367A), acridine and phenazine compounds (described in JP1985-105667A (JP-S60-105667A) and U.S. Pat. No. 4,239,850A), oxadiazole compounds (described in U.S. Pat. No. 4,212,970A), and acyl phosphine oxide compounds (described in JP1988-040799B (JP-S63-040799B), JP1993-029234B (JP-H05-029234B), JP1998-095788A (JP-H10-095788A), and JP1998-029997A (JP-H10-029997A)).

In the present invention, for a reason that the moisture-heat resistance of the optically anisotropic film formed is further improved, the polymerization initiator is preferably an oxime-type polymerization initiator, and specifically, a polymerization initiator represented by Formula (PI) is more preferable.

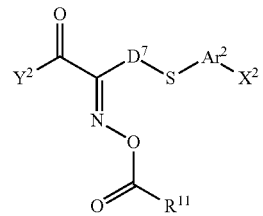

(PI)

In Formula (PI), $X^2$ represents a hydrogen atom or a halogen atom.

Furthermore, in Formula (PI), $Ar^2$ represents a divalent aromatic group and $D^7$ represents a divalent organic group having 1 to 12 carbon atoms.

In addition, in Formula (PI), $R^{11}$ represents an alkyl group having 1 to 12 carbon atoms and $Y^2$ represents a monovalent organic group.

In Formula (PI), examples of the halogen atom represented by $X^2$ include a fluorine atom, a chlorine atom, a bromine atom, and an iodine atom, and among these, the chlorine atom is preferable.

Furthermore, in Formula (PI), examples of the divalent aromatic group represented by $Ar^2$ include divalent groups having an aromatic hydrocarbon ring such as a benzene ring, a naphthalene ring, an anthracene ring, and a phenanthroline ring; and divalent groups having an aromatic heterocyclic ring, such as a furan ring, a pyrrole ring, a thiophene ring, a pyridine ring, a thiazole ring, and a benzothiazole ring.

Incidentally, in Formula (PI), examples of the divalent organic group having 1 to 12 carbon atoms represented by $D^7$ include a linear or branched alkylene group having 1 to 12 carbon atoms, and specific suitable examples thereof include a methylene group, an ethylene group, and a propylene group.

Moreover, in Formula (PI), specific suitable examples of the alkyl group having 1 to 12 carbon atoms represented by $R^{11}$ include a methyl group, an ethyl group, and a propyl group.

In addition, in Formula (PI), examples of the monovalent organic group represented by $Y^2$ include a functional group including a benzophenone skeleton $((C_6H_5)_2CO)$. Specifically, in a similar manner to groups represented by Formula (PIa) and Formula (PIb), a functional group including a benzophenone skeleton in which a benzene ring at the terminal is unsubstituted or mono-substituted is preferable. Further, in Formula (PIa) and Formula (PIb), * represents a bonding position, and that is, a bonding position to the carbon atom of the carbonyl group in Formula (PI).

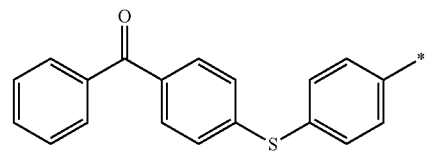

(PIa)

-continued

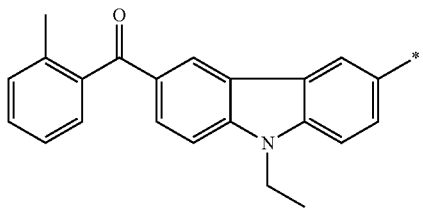

(PIb)

Examples of the oxime-type polymerization initiator represented by Formula (PI) include a compound represented by Formula (PI-1) and a compound represented by Formula (PI-2).

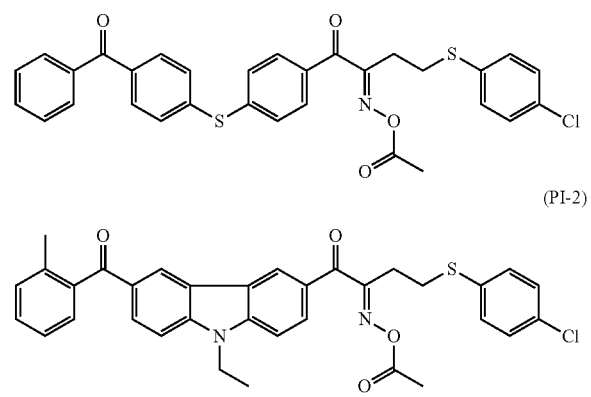

(PI-1)

(PI-2)

In the present invention, the content of the polymerization initiator is not particularly limited, but is preferably 0.01% to 20% by mass, and more preferably 0.5% to 5% by mass of the solid content of the polymerizable liquid crystal composition.

[Solvent]

It is preferable that the polymerizable liquid crystal composition of the embodiment of the present invention contains a solvent from the viewpoint of workability for forming an optically anisotropic film, and the like.

Specific examples of the solvent include ketones (for example, acetone, 2-butanone, methyl isobutyl ketone, cyclohexanone, and cyclopentanone), ethers (for example, dioxane and tetrahydrofuran), aliphatic hydrocarbons (for example, hexane), alicyclic hydrocarbons (for example, cyclohexane), aromatic hydrocarbons (for example, toluene, xylene, and trimethylbenzene), halogenated carbons (for example, dichloromethane, dichloroethane, dichlorobenzene, and chlorotoluene), esters (for example, methyl acetate, ethyl acetate, and butyl acetate), water, alcohols (for example, ethanol, isopropanol, butanol, and cyclohexanol), cellosolves (for example, methyl cellosolve and ethyl cellosolve), cellosolve acetates, sulfoxides (for example, dimethyl sulfoxide), and amides (for example, dimethylformamide and dimethylacetamide), and these may be used singly or in combination of two or more kinds thereof.

[Leveling Agent]

It is preferable that the polymerizable liquid crystal composition of the embodiment of the present invention contains a leveling agent from the viewpoint that the surface of an optically anisotropic film is maintained smooth and the alignment is easily controlled.

Such a leveling agent is preferably a fluorine-based leveling agent or a silicon-based leveling agent for a reason that it has a high leveling effect on the addition amount, and the leveling agent is more preferably a fluorine-based leveling agent from the viewpoint that it is less likely to cause bleeding (bloom or bleed).

Specific example of the leveling agent include the compounds described in paragraphs 0079 to 0102 of JP2007-069471A, the compound represented by General Formula (I) described in JP2013-047204A (in particular, the compounds described in paragraphs 0020 to 0032), the compound represented by General Formula (I) described in JP2012-211306A (in particular, the compounds described in paragraphs 0022 to 0029), the liquid crystal alignment accelerator represented by General Formula (I) described in JP2002-129162A (in particular, the compounds described in paragraphs 0076 to 0078 and 0082 to 0084), and the compounds represented by General Formulae (I), (II), and (III) described in JP2005-099248A (in particular, the compounds described in paragraphs 0092 to 0096). In addition, the leveling agent may also function as an alignment control agent which will be described later.

[Alignment Control Agent]

The polymerizable liquid crystal composition of the embodiment of the present invention can contain an alignment control agent, as desired.

With the alignment control agent, various alignment states such as homeotropic alignment (vertical alignment), tilt alignment, hybrid alignment, and cholesteric alignment can be formed, in addition to the homogeneous alignment, and specific alignment states can be controlled and achieved more uniformly and more accurately.

As an alignment control agent that accelerates the homogeneous alignment, for example, a low-molecular-weight alignment control agent or a high-molecular-weight alignment control agent can be used.

With regard to the low-molecular-weight alignment control agent, reference can be made to the description in, for example, paragraphs 0009 to 0083 of JP2002-020363A, paragraphs 0111 to 0120 of JP2006-106662A, and paragraphs 0021 to 0029 of JP2012-211306A, the contents of which are incorporated herein by reference.

In addition, with regard to the high-molecular-weight alignment control agent, reference can be made to the description in, for example, paragraphs 0021 to 0057 of JP2004-198511A and paragraphs 0121 to 0167 of JP2006-106662A, the contents of which are incorporated herein by reference.

Furthermore, examples of the alignment control agent that forms or accelerates the homeotropic alignment include a boronic acid compound and an onium salt compound, and specifically, reference can be made to the compounds described in paragraphs 0023 to 0032 of JP2008-225281A, paragraphs 0052 to 0058 of JP2012-208397A, paragraphs 0024 to 0055 of JP2008-026730A, paragraphs 0043 to 0055 of JP2016-193869A, and the like, the contents of which are incorporated herein by reference.

On the other hand, the cholesteric alignment can be achieved by adding a chiral agent to the polymerizable liquid crystal composition of the embodiment of the present invention, and it is possible to control the direction of revolution of the cholesteric alignment by its chiral direction. Incidentally, it is possible to control the pitch of the cholesteric alignment in accordance with the alignment regulating force of the chiral agent.

In a case where an alignment control agent is contained, a content of the alignment control agent is preferably 0.01% to 10% by mass, and more preferably 0.05% to 5% by mass, with respect to the mass of the total solid content of the polymerizable liquid crystal composition. In a case where the content is within the range, it is possible to obtain an optically anisotropic film which has no precipitation or phase separation, alignment defects, or the like, and is uniform and highly transparent while achieving a desired alignment state.

These alignment control agents can further impart a polymerizable functional group, in particular, a polymerizable functional group which is polymerizable with a polymerizable liquid crystal compound constituting the polymerizable liquid crystal composition of the embodiment of the present invention.

[Ultraviolet Absorber]

The polymerizable liquid crystal composition of the embodiment of the present invention may contain an ultraviolet absorber represented by Formula (5).

In addition, it is preferable that a maximum absorption wavelength A of the polymerizable liquid crystal compound represented by Formula (1) and a maximum absorption wavelength B of the ultraviolet absorber represented by Formula (5) satisfy Formula (6).

Here, in the present specification, the maximum absorption wavelength refers to an absorption wavelength on the longest wavelength side of peaks present in a wavelength range of 300 to 400 nm, and for example, in a case where the absorption spectrum shows twin peaks, an absorption on the long wavelength side is taken as the maximum absorption wavelength.

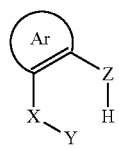

(5)

$$0 \text{ nm} \leq A\text{-}B < 24 \text{ nm}$$ (6)

In Formula (5), Ar represents an aromatic hydrocarbon ring or aromatic heterocyclic ring, which may have a substituent.

Here, examples of the aromatic hydrocarbon ring include aryl groups such as a phenyl group, a 2,6-diethylphenyl group, and a naphthyl group.

Moreover, examples of the aromatic heterocyclic ring include heteroaryl groups such as a thienyl group, a thiazolyl group, a furyl group, and a pyridyl group.

Furthermore, examples of the substituent which may be contained in Ar include an alkyl group, an alkoxy group, and a halogen atom.

As the alkyl group, for example, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a t-butyl group, and a cyclohexyl group) is more preferable, an alkyl group having 1 to 4 carbon atoms is still more preferable, and the methyl group or the ethyl group is particularly preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, and a methoxy ethoxy group) is more preferable, an alkoxy group having 1 to 4 carbon atoms is still more preferable, and the methoxy group or the ethoxy group is particularly preferable.

Examples of the halogen atom include a fluorine atom, a chlorine atom, a bromine atom, and an iodine atom, and among these, the fluorine atom or the chlorine atom is preferable.

Furthermore, in Formula (5), X represents a carbon atom or a nitrogen atom, Y represents an oxygen atom or a nitrogen atom, Z represents an oxygen atom or a nitrogen atom, X, Y, and Z may each have a substituent, and a substituent contained in X and a substituent contained in Y may be bonded to each other to form a ring including X and Y. It should be noted that the bonding type between X and Y may be either a double bond or a triple bond, depending on the presence or absence of the substituent of Y.

Examples of the substituent which may be contained in each of X, Y, and Z include the same ones as the substituents which may be contained in Ar.

Examples of the ultraviolet absorber represented by Formula (5) include compounds described in paragraphs 0018 to 0031 of JP2007-072163A, and specifically, compounds described in paragraphs 0055 to 0105 of the same publication.

Other examples of the ultraviolet absorber represented by Formula (5) include triazine-based compounds described in paragraphs 0011 to 0041 of JP2013-082707A.

In addition, as a commercially available product of the ultraviolet absorber represented by Formula (5), Tinuvin 400, Tinuvin 405, Tinuvin 460, Tinuvin 477, Tinuvin 479, or Tinuvin 1577 (all manufactured by BASF), or the like can be used.

In the present invention, for a reason that the light resistance of the optically anisotropic film formed is improved, the content of the ultraviolet absorber represented by Formula (5) in a case where it is contained in the optically anisotropic film is preferably 1% to 20% by mass with respect to the content of the polymerizable liquid crystal compound represented by Formula (1).

The reason why the light resistance is improved is not clear, but it is presumed that in a case where a maximum absorption wavelength A of the polymerizable liquid crystal compound and a maximum absorption wavelength B of the ultraviolet absorber satisfy Formula (6), there are more regions where the absorption wavelength of the polymerizable liquid crystal compound and the ultraviolet absorber overlap, and thus, energy transfer from the polymerizable liquid crystal compound to the ultraviolet absorber easily occurs. As a result, it is presumed that decomposition of the polymerizable liquid crystal compound is suppressed, and thus, the light resistance of the optically anisotropic film is improved.

[Optically Anisotropic Film]

An optically anisotropic film of an embodiment of the present invention is an optically anisotropic film obtained by polymerization of the above-mentioned polymerizable liquid crystal composition of the embodiment of the present invention.

Examples of a method for forming the optically anisotropic film include a method in which the above-mentioned polymerizable liquid crystal composition of the embodiment of the present invention is used to form a desired alignment state, which is then fixed by polymerization.

Here, the polymerization conditions are not particularly limited, but in the polymerization by irradiation with light, ultraviolet rays are preferably used. The irradiation dose is preferably 10 mJ/cm$^2$ to 50 J/cm$^2$, more preferably 20 mJ/cm² to 5 J/cm², still more preferably 30 mJ/cm² to 3 J/cm², and particularly preferably 50 mJ/cm² to 1,000 mJ/cm². In addition, the polymerization may be carried out under a heating condition in order to accelerate the polymerization reaction.

In addition, in the present invention, the optically anisotropic film can be formed on any of supports in the optical film of the embodiment of the present invention which will be described later or a polarizer in the polarizing plate of an embodiment of the present invention which will be described later.

In the present invention, for a reason that a contrast ratio in an image display device, particularly a liquid crystal display device is enhanced, it is preferable that the optically anisotropic film is a film obtained by aligning the above-mentioned polymerizable liquid crystal composition of the embodiment of the present invention into a smectic phase and then performing polymerization (fixing of the alignment).

This is considered to result from suppression of scattering caused by the alignment disorder of the optically anisotropic layer due to a higher order of the smectic phase than that of a nematic phase. In addition, whether the optically anisotropic film exhibits the smectic phase or not is determined by X-ray diffraction, depending on whether the film has a periodic structure or not. For example, the presence or absence of the periodic structure can be confirmed by analyzing a diffraction pattern with an X-ray thin-film diffractometer ATXG (manufactured by Rigaku).

The optically anisotropic film of the embodiment of the present invention is preferably a positive A-plate or a positive C-plate, and more preferably the positive A-plate.

Here, the positive A-plate (A-plate which is positive) and the positive C-plate (C-plate which is positive) are defined as follows.

In a case where a refractive index in a film in-plane slow axis direction (in a direction in which an in-plane refractive index is maximum) is defined as nx, a refractive index in an in-plane direction orthogonal to the in-plane slow axis is defined as ny, and a refractive index in a thickness direction is defined as nz, the positive A-plate satisfies the relationship of Formula (A1) and the positive C-plate satisfies the relationship of Formula (C1). In addition, the positive A-plate has an Rth showing a positive value and the positive C-plate has an Rth showing a negative value.

$nx > ny \approx nz$  Formula (A1)

$nz > nx \approx ny$  Formula (C1)

Furthermore, the symbol "≈" encompasses not only a case where the both are completely the same as each other but also a case where the both are substantially the same as each other.

The expression "substantially the same" means that with regard to the positive A-plate, for example, a case where (ny−nz)×d (in which d is the thickness of a film) is −10 to 10 nm, preferably −5 to 5 nm, is also included in "ny≈nz", and a case where (nx−nz)×d is −10 to 10 nm, preferably −5 to 5 nm, is also included in "nx≈nz". In addition, with regard to the positive C-plate, for example, a case where (nx−ny)×d (in which d is the thickness of a film) is 0 to 10 nm, preferably 0 to 5 nm, is also included in "nx≈ny".

In a case where the optically anisotropic film of the embodiment of the present invention is a positive A-plate, the Re(550) is preferably 100 to 180 nm, more preferably 120 to 160 nm, still more preferably 130 to 150 nm, and particularly preferably 130 to 140 nm, from the viewpoint that the optically anisotropic film functions as a λ/4 plate.

Here, the terms "λ/4 plate" is a plate having a λ/4 function, specifically, a plate having a function of converting a linearly polarized light at a certain specific wavelength into a circularly polarized light (or converting a circularly polarized light to a linearly polarized light).

[Optical Film]

The optical film of the embodiment of the present invention is an optical film having the optically anisotropic film of the embodiment of the present invention.

Figure 1B:
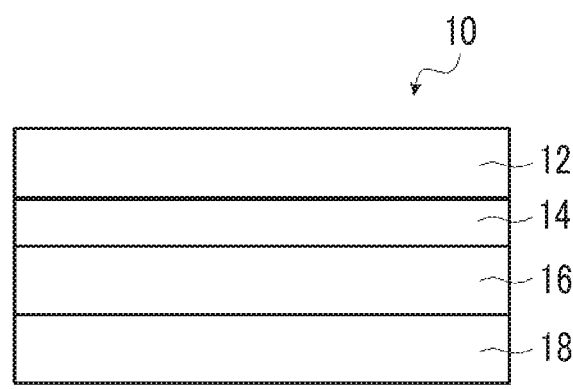
FIG. 1B is a schematic cross-sectional view showing an example of the optical film of an embodiment of the present invention.
Figure 1C:
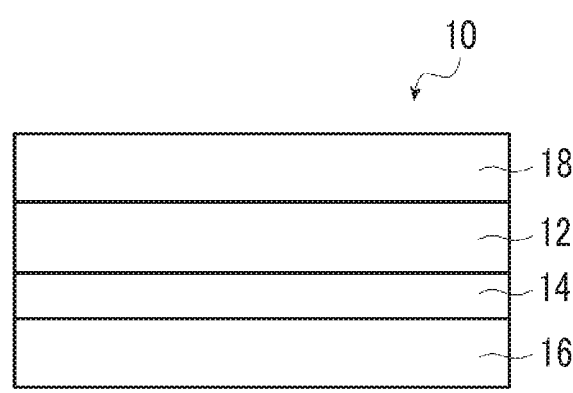
FIG. 1C is a schematic cross-sectional view showing an example of the optical film of an embodiment of the present invention.

FIG. 1A, FIG. 1B, and FIG. 1C (hereinafter, these drawings are simply referred to as "FIG. 1" unless it is necessary that they are particularly distinguished from each other) are each a schematic cross-sectional view showing an example of the optical film of the embodiment of the present invention.

Furthermore, FIG. 1 is a schematic view, and the thicknesses relationship, the positional relationship, and the like among the respective layers are not necessarily consistent with actual ones, and any of the support, the alignment film, and the hard coat layer shown in FIG. 1 are optional constitutional members.

An optical film 10 shown in FIG. 1 has a support 16, an alignment film 14, and an optically anisotropic film 12 in this order.

In addition, the optical film 10 may have a hard coat layer 18 on the side of the support 16 opposite to the side on which the alignment film 14 is provided as shown in FIG. 1B, and may have the hard coat layer 18 on the side of the optically anisotropic film 12 opposite to the side on which the alignment film 14 is provided as shown in FIG. 1C.

Hereinafter, various members used for the optical film of the embodiment of the present invention will be described in detail.

[Optically Anisotropic Film]

The optically anisotropic film contained in the optical film of the embodiment of the present invention is the above-mentioned optically anisotropic film of the embodiment of the present invention.

In the optical film of the embodiment of the present invention, the thickness of the optically anisotropic film is not particularly limited, but is preferably 0.1 to 10 μm, and more preferably 0.5 to 5 μm.

[Support]

The optical film of the embodiment of the present invention may have a support as a base material for forming an optically anisotropic film as described above. Such a support is preferably transparent, and specifically, the support preferably has a light transmittance of 80% or more.

Examples of such a support include a glass substrate and a polymer film, and examples of the material for the polymer film include cellulose-based polymers; acrylic polymers having acrylic acid ester polymers such as polymethyl methacrylate and a lactone ring-containing polymer, thermoplastic norbornene-based polymers; polycarbonate-based polymers; polyester-based polymers such as polyethylene terephthalate and polyethylene naphthalate; styrene-based polymers such as polystyrene and an acrylonitrile-styrene copolymer (AS resin); polyolefin-based polymers such as polyethylene, polypropylene, and an ethylene-propylene copolymer, vinyl chloride-based polymers; amide-based polymers such as nylon and aromatic polyamide; imide-based polymers; sulfone-based polymers; polyether sulfone-based polymers; polyether ether ketone-based polymers; polyphenylene sulfide-based polymers; vinylidene chloride-based polymers; vinyl alcohol-based polymers; vinyl butyral-based polymers; acrylate-based polymers; polyoxymethylene-based polymers; epoxy-based polymers; and polymers obtained by mixing these polymers.

In addition, an aspect in which a polarizer which will be described later may also function as such a support is also available.

In the present invention, the thickness of the support is not particularly limited, but is preferably 5 to 60 µm, and more preferably 5 to 30 µm.

[Alignment Film]

In a case where the optical film of the embodiment of the present invention has any of the above-mentioned supports, it is preferable that the optical film has an alignment film between the support and the optically anisotropic film. Further, an aspect in which the above-mentioned support may also function as an alignment film is also available.

The alignment film generally has a polymer as a main component. The polymer materials for an alignment film are described in numerous documents, and many commercially available products can be used.

The polymer material used in the present invention is preferably a polyvinyl alcohol or a polyimide, or a derivative thereof. Particularly, a modified or non-modified polyvinyl alcohol is preferable.

Examples of the alignment film that can be used in the present invention include alignment films described in Line 24 on Page 43 to Line 8 on Page 49 of WO01/088574A; modified polyvinyl alcohols described in paragraphs 0071 to 0095 of JP3907735B; and a liquid crystal alignment film formed by a liquid crystal aligning agent described in JP2012-155308A.

In the present invention, for a reason that it is possible to prevent deterioration in the surface state by avoiding a contact with the surface of an alignment film upon formation of the alignment film, a photoalignment film is also preferably used as the alignment film.

The photoalignment film is not particularly limited, but polymer materials such as a polyamide compound and a polyimide compound, described in paragraphs 0024 to 0043 of WO2005/096041A; a liquid crystal alignment film formed by a liquid crystal aligning agent having a photoaligned group, described in JP2012-155308A; LPP-JP265CP, product name, manufactured by Rolic technologies Ltd.; or the like can be used.

In addition, in the present invention, the thickness of the alignment film is not particularly limited, but from the viewpoint of forming an optically anisotropic film having a uniform film thickness by alleviating the surface roughness that can be present on the support, the thickness is preferably 0.01 to 10 µm, more preferably 0.01 to 1 µm, and still more preferably 0.01 to 0.5 µm.

[Hard Coat Layer]

It is preferable that the optical film of the embodiment of the present invention has a hard coat layer in order to impart physical strength to the film. Specifically, the optical film may have the hard coat layer on the side of the support opposite to the side on which the alignment film is provided (refer to FIG. 1B) or the optical film may have the hard coat layer on the side of the optically anisotropic film opposite to the side on which the alignment film is provided (refer to FIG. 1C).

As the hard coat layer, those described in paragraphs 0190 to 0196 of JP2009-098658A can be used.

[Other Optically Anisotropic Films]

The optical film of the embodiment of the present invention may have other optically anisotropic films, in addition to the optically anisotropic film of the embodiment of the present invention.

That is, the optical film of the embodiment of the present invention may have a laminated structure having the optically anisotropic film of the embodiment of the present invention and other optically anisotropic films.

Such other optically anisotropic films are not particularly limited as long as the optically anisotropic films are obtained by not blending the polymerizable liquid crystal compound represented by Formula (1), but using the above-mentioned other polymerizable compounds (in particular, liquid crystal compounds).

Here, the liquid crystal compounds can be generally classified into a rod-shaped type and a disk-shaped type according to the shape thereof. Each of the types can further be classified into a low-molecular-weight type and a high-molecular-weight type. The term, high-molecular-weight, generally refers to having a degree of polymerization of 100 or more (Polymer Physics-Phase Transition Dynamics, by Masao Doi, page 2, published by Iwanami Shoten, Publishers, 1992). In the present invention, any of the liquid crystal compounds can be used, but the rod-shaped liquid crystal compound or the discotic liquid crystal compound (disk-shaped liquid crystal compound) is preferably used. A mixture of two or more kinds of the rod-shaped liquid crystal compounds, two or more kinds of the disk-shaped liquid crystal compounds, or the rod-shaped liquid crystal compound and the disk-shaped liquid crystal compound may be used. In order to fix the above-mentioned liquid crystal compound, it is more preferable that the liquid crystal compound is formed of a rod-shaped liquid crystal compound or disk-shaped liquid crystal compound having a polymerizable group, and it is still more preferable that the liquid crystal compound has two or more polymerizable groups in one molecule. In a case of a mixture of two or more kinds of the liquid crystal compounds, at least one kind of the liquid crystal compound preferably has two or more polymerizable groups in one molecule.

As the rod-shaped liquid crystal compound, for example, the rod-shaped liquid crystal compounds described in claim 1 of JP1999-513019A (JP-H1-513019A) or paragraphs 0026 to 0098 of JP2005-289980A can be preferably used, and as the discotic liquid crystal compound, for example, the discotic liquid crystal compounds described in paragraphs 0020 to 0067 of JP2007-108732A and paragraphs 0013 to 0108 of JP2010-244038A can be preferably used, but the liquid crystal compounds are not limited thereto.

[Polarizing Plate]

A polarizing plate of an embodiment of the present invention has the above-mentioned optical film of the embodiment of the present invention and a polarizer.

Furthermore, in a case where the above-mentioned optically anisotropic film of the embodiment of the present invention is λ/4 plate (positive A-plate), the polarizing plate of the embodiment of the present invention can be used as a circularly polarizing plate.

In addition, in a case where the above-mentioned optically anisotropic film of the embodiment of the present invention is a λ/4 plate (positive A-plate), an angle between the slow axis of the λ/4 plate and the absorption axis of a polarizer which will be described later is preferably 300 to 600, more preferably 400 to 500, still more preferably 420 to 480, and particularly preferably 45° in the polarizing plate of the embodiment of the present invention.

Here, the terms "slow axis" of the λ/4 plate means a direction in which the refractive index in the plane of the λ/4 plate becomes maximum, and the terms "absorption axis" of the polarizer means a direction in which the absorbance is highest.

[Polarizer]

A polarizer contained in the polarizing plate of the embodiment of the present invention is not particularly limited as long as it is a member having a function of converting light into specific linearly polarized light, and an absorptive type polarizer and a reflective type polarizer, which are known in the related art, can be used.

An iodine-based polarizer, a dye-based polarizer using a dichroic dye, a polyene-based polarizer, or the like is used as the absorptive type polarizer. The iodine-based polarizer and the dye-based polarizer are classified into a coating type polarizer and a stretching type polarizer, any of which can be applied, but a polarizer which is manufactured by allowing polyvinyl alcohol to adsorb iodine or a dichroic dye and performing stretching is preferable.

In addition, examples of a method of obtaining a polarizer by carrying out stretching and dyeing in a state of a laminated film in which a polyvinyl alcohol layer is formed on a base material include the methods described in JP5048120B, JP5143918B, JP4691205B, JP4751481B, and JP4751486B, and known technologies relating to these polarizers can also be preferably used.

A polarizer in which thin films having different birefringence are laminated, a wire grid-type polarizer, a polarizer having a combination of a cholesteric liquid crystal having a selective reflection range and a ¼ wavelength plate, or the like is used as the reflective type polarizer.

Among those, a polarizer including a polyvinyl alcohol-based resin (a polymer including —$CH_2$—CHOH— as a repeating unit, in particular, at least one selected from the group consisting of a polyvinyl alcohol and an ethylene-vinyl alcohol copolymer) is preferable from the viewpoint that the adhesiveness is more excellent.

In the present invention, the thickness of the polarizer is not particularly limited, but is preferably 3 μm to 60 μm, more preferably 5 μm to 30 μm, and still more preferably 5 μm to 15 μm.

[Pressure-Sensitive Adhesive Layer]

The polarizing plate of the embodiment of the present invention may have a pressure-sensitive adhesive layer arranged between the optically anisotropic film in the optical film of the embodiment of the present invention and the polarizer.

The pressure-sensitive adhesive layer used for lamination of the optically anisotropic film and the polarizer represents, for example, a substance in which a ratio (tan δ=G"/G') between a storage elastic modulus G' and a loss elastic modulus G", each measured with a dynamic viscoelastometer, is 0.001 to 1.5, and examples thereof include a so-called pressure-sensitive adhesive or readily creepable substance. Examples of the pressure-sensitive adhesive that can be used in the present invention include a polyvinyl alcohol-based pressure-sensitive adhesive, but the pressure-sensitive adhesive is not limited thereto.

[Image Display Device]

An image display device of an embodiment of the present invention is an image display device having the optical film of the embodiment of the present invention or the polarizing plate of the embodiment of the present invention.

A display element used in the image display device of the embodiment of the present invention is not particularly limited, and examples thereof include a liquid crystal cell, an organic electroluminescent (hereinafter abbreviated as "EL") display panel, and a plasma display panel.

Among these, the liquid crystal cell or the organic EL display panel is preferable, and the liquid crystal cell is more preferable. That is, as the image display device of the embodiment of the present invention, a liquid crystal display device using a liquid crystal cell as a display element or an organic EL display device using an organic EL display panel as a display element is preferable, and the liquid crystal display device is more preferable.

[Liquid Crystal Display Device]

A liquid crystal display device that is an example of the image display device of the embodiment of the present invention is a liquid crystal display device having the above-mentioned polarizing plate of the embodiment of the present invention and a liquid crystal cell.

In addition, in the present invention, it is preferable that the polarizing plate of the embodiment of the present invention is used as a polarizing plate of the front side, out of the polarizing plates provided on the both sides of the liquid crystal cell, and it is more preferable that the polarizing plate of the embodiment of the present invention is used as polarizing plates on the front and rear sides.

Hereinafter, the liquid crystal cell constituting the liquid crystal display device will be described in detail.

<Liquid Crystal Cell>

A liquid crystal cell for use in the liquid crystal display device is preferably in a vertical alignment (VA) mode, an optically compensated bend (OCB) mode, an in-plane-switching (IPS) mode, or a twisted nematic (TN) mode, but the liquid crystal cell is not limited thereto.

In a TN-mode liquid crystal cell, rod-shaped liquid crystal molecules are substantially horizontally aligned and are twist-aligned at 60° to 120° during no voltage application thereto. A TN-mode liquid crystal cell is most often used in a color TFT liquid crystal display device and described in numerous documents.

In a VA-mode liquid crystal cell, rod-shaped liquid crystal molecules are substantially vertically aligned during no voltage application thereto. Examples of the VA-mode liquid crystal cell include (1) a VA-mode liquid crystal cell in the narrow sense of the word, in which rod-shaped liquid crystal molecules are substantially vertically aligned during no voltage application thereto, but are substantially horizontally aligned during voltage application thereto (described in JP1990-176625A (JP-H02-176625A)), (2) an (MVA-mode) liquid crystal cell in which the VA mode is multi-domained for viewing angle enlargement (described in SID97, Digest of Tech. Papers (preprint), 28 (1997) 845), (3) a liquid crystal cell in a mode (n-ASM mode) in which rod-shaped liquid crystal molecules are substantially vertically aligned during no voltage application thereto and are multi-domain-aligned during voltage application thereto (described in preprint of Seminar of Liquid Crystals of Japan, 58 and 59 (1998)), and (4) a survival-mode liquid crystal cell (announced in LCD International 98). In addition, the liquid crystal cell may be of any of a patterned vertical alignment (PVA) type, an optical alignment type, and a polymer-sustained alignment (PSA) type. Details of these modes are specifically described in JP2006-215326A and JP2008-538819A.

In an IPS-mode liquid crystal cell, rod-shaped liquid crystal molecules are aligned substantially parallel with respect to a substrate, and application of an electric field parallel to the substrate surface causes the liquid crystal molecules to respond planarly. The IPS mode displays black in a state where no electric field is applied and a pair of upper and lower polarizing plates have absorption axes which are orthogonal to each other. A method of improving the viewing angle by reducing light leakage during black display in an oblique direction using an optical compensation sheet is disclosed in JP1998-054982A (JP-H10-054982A), JP1999-202323A (JP-H11-202323A), JP1997-292522A (JP-H09-292522A), JP1999-133408A (JP-H11-133408A), JP1999-305217A (JP-H11-305217A), JP1998-307291A (JP-H10-307291A), and the like.

[Organic EL Display Device]

Suitable examples of the organic EL display device which is an example of the image display device of the embodiment of the present invention include an aspect which includes, from the visible side, a polarizer, a λ/4 plate (positive A-plate) consisting of the optically anisotropic film of the embodiment of the present invention, and an organic EL display panel in this order.

Furthermore, the organic EL display panel is a display panel constituted with an organic EL element in which an organic light emitting layer (organic electroluminescent layer) is sandwiched between electrodes (between a cathode and an anode). The configuration of the organic EL display panel is not particularly limited but any known configurations are adopted.

EXAMPLES

Hereinafter, the present invention will be described in more detail with reference to Examples. The materials, the amounts of materials used, the proportions, the treatment details, the treatment procedure, and the like shown in Examples below can be appropriately modified as long as the modifications do not depart from the spirit of the present invention. Therefore, the scope of the present invention should not be construed as being limited to Examples shown below.

[Synthesis of Compound (I-1a)]

A compound (I-1a) represented by Formula (I-1a) was synthesized with reference to the method described in paragraphs 0161 and 0162 of JP2010-254949A.

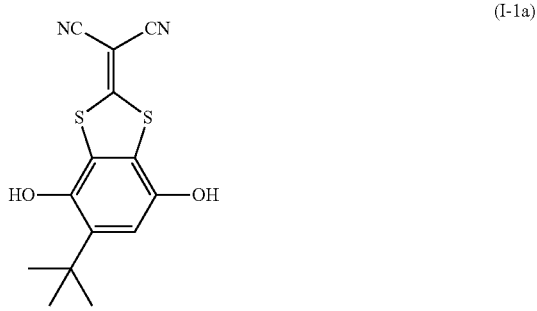 [SMILES: CC(C)(C)c1cc(O)c2c(c1O)SC(=C(C#N)C#N)S2]

(I-1a)

Specifically, 26.1 g (400 mmol) of 86% potassium hydroxide was dissolved in 80 ml of isopropyl alcohol and 45 ml of water under a nitrogen stream. A solution prepared by dissolving 13.21 g (200 mmol) of malononitrile in 10 ml of isopropyl alcohol was added to this solution under ice cooling and stirring at the internal temperature of 5° C. or lower. Subsequently, 15.23 g (200 mmol) of carbon disulfide was added dropwise thereto at an internal temperature of 10° C. or lower, and then the mixture was stirred for 30 minutes under ice cooling. 3.43 ml (60 mmol) of acetic acid was added to the reaction solution to adjust pH of the solution to 6, and then a mixed solution of 71.07 g (purity: 88%, 380 mmol) of 2-t-butyl-1,4-benzoquinone, 22.9 ml (400 mmol) of acetic acid, and 290 ml of acetone were slowly added dropwise thereto while keeping the internal temperature at 2° C. or lower. After stirring the mixture at the same temperature for 30 minutes, the temperature thereof was raised to 25° C., 40 ml of water was added thereto, the mixture was stirred and allowed to stand, and the separated lower layer was removed. After raising the internal temperature to 40° C. to 45° C., a mixed solution of 130 ml of acetonitrile and 130 ml of water was added dropwise thereto, and the mixture was stirred at the same temperature for 30 minutes to cause precipitation of crystals. Thereafter, 130 ml of water was further added thereto, the mixture was cooled to 20° C., and then the precipitated crystals were collected by filtration and washed with a mixed solution of 130 ml of acetonitrile and 130 ml of water. The obtained crystals were dried at 50° C. under reduced pressure to obtain 47.6 g (yield: 79%) of a compound (I-1a) as a pale yellow solid.

[Synthesis of Compound (I-1c)]

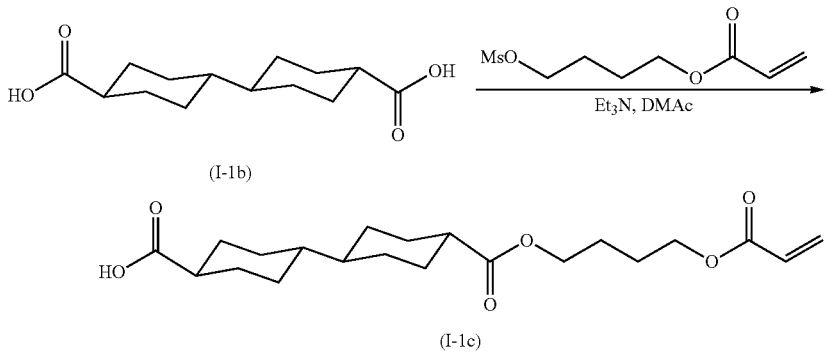

(I-1b)

(I-1c)

As shown in the scheme, 10.0 g (39.3 mmol) of a compound (I-1b), 50 ml of N,N-dimethylacetamide (DMAc), 8.0 ml (78.6 mmol) of triethylamine, and 433 mg of 2,6-di-t-butyl-4-methylphenol were mixed at room temperature (23° C.).

9.61 g (43.2 mmol) of 4-methylsulfonyloxybutyl acrylate was added to the mixture, and the mixture was stirred at 100° C. for 5 hours. After cooling to room temperature, 30 ml of a 1 N aqueous hydrochloric acid solution and 50 ml of toluene were added thereto, and the mixture was stirred at 40° C. and then subjected to liquid separation. The organic layer was washed with a 5% aqueous sodium hydrogen carbonate solution, a 1% aqueous sodium hydrogen carbonate solution, and a 1% aqueous sodium hydrogen carbonate solution in this order, 20 mg of 2,2,6,6-tetramethylpiperidin-1-oxyl (TEMPO) was added thereto, and then the solvent was evaporated under reduced pressure. The residue was recrystallized with ethanol/toluene/n-hexane to obtain 4.78 g (12.6 mmol) of a carboxylic acid derivative (I-1c) (yield: 32%). In addition, all the aqueous layers during liquid separation were combined and hydrochloric acid was added dropwise thereto until the liquid became acidic, thereby precipitating an unreacted compound (I-1b), which was collected by filtration. This crude product was added to 10 ml of acetone, and the mixture was stirred for 30 minutes and then collected by filtration to recover 1.6 g of a compound (I-1b) (recovery rate: 16%).

The $^1$H-nuclear magnetic resonance (NMR) of the obtained compound (I-1c) is shown below.

$^1$H-NMR (solvent: CDCl$_3$) δ (ppm): 1.0-1.1 (m, 6H), 1.3-1.5 (m, 4H), 1.7-1.8 (m, 8H), 2.0-2.1 (m, 4H), 2.2 (tt, 1H), 2.2 (tt, 1H), 4.1 (t, 2H), 4.2 (t, 2H), 5.8 (dd, 1H), 6.1 (dd, 1H), 6.4 (dd, 1H)

[Synthesis of Compound (I-1d)]

As shown in the scheme, 10.0 g (39.3 mmol) of the compound (I-1b), 100 ml of ethyl acetate (EA), 18.2 ml of N,N-dimethylacetamide (DMAc), and 433 mg of 2,6-di-t-butyl-4-methylphenol were mixed at room temperature, and the internal temperature was lowered to 5° C. 6.24 ml (86.5 mmol) of thionyl chloride (SOCl$_2$) was added dropwise to the mixture while the internal temperature was maintained below 10° C. After stirring at 5° C. for 1 hour, 6.77 g (39.3 mmol) of 5-hydroxy-3-methylpentyl acrylate was added to the mixture. 37.7 ml (216 mmol) of N,N-diisopropylethylamine (DIPEA) was added dropwise thereto and the mixture was stirred at room temperature for 2 hours. After stirring,

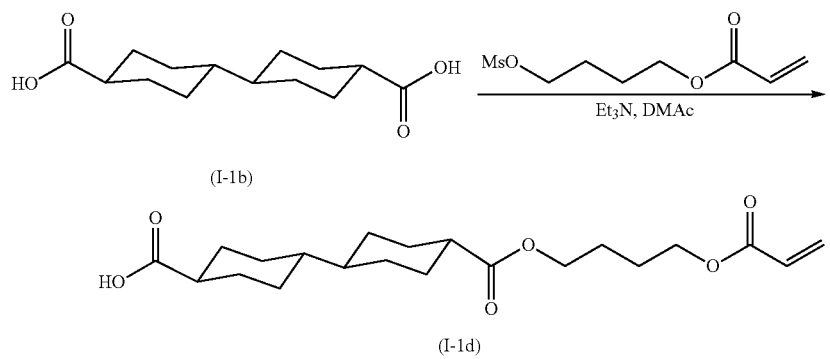

As shown in the scheme, 10.0 g (39.3 mmol) of a compound (I-1b), 50 ml of N,N-dimethylacetamide (DMAc), 8.0 ml (78.6 mmol) of triethylamine, and 433 mg of 2,6-di-t-butyl-4-methylphenol were mixed at room temperature (23° C.).

9.85 g (39.3 mmol) of 6-methylsulfonyloxyhexyl acrylate was added to the mixture, and the mixture was stirred at 100° C. for 5 hours. After cooling to room temperature, 30 ml of a 1 N aqueous hydrochloric acid solution and 50 ml of toluene were added thereto, and the mixture was stirred at 40° C. and then subjected to liquid separation. The organic layer was washed with a 5% aqueous sodium hydrogen carbonate solution, a 1% aqueous sodium hydrogen carbonate solution, and a 1% aqueous sodium hydrogen carbonate solution in this order, 20 mg of 2,2,6,6-tetramethylpiperidin-1-oxyl (TEMPO) was added thereto, and then the solvent was evaporated under reduced pressure. The obtained compound (I-1d) was used in the next step as a toluene solution without further purification.

[Synthesis of Compound (I-1e)]

100 ml of a 1 N aqueous hydrochloric acid solution was added thereto to stop the reaction and the mixture was subjected to liquid separation. The organic layer was washed with a 10% saline solution and then dried over magnesium sulfate, 20 mg of 2,2,6,6-tetramethylpiperidin-1-oxyl (TEMPO) was added thereto, and then the solvent was evaporated under reduced pressure. The obtained crude product was purified by silica gel column chromatography to obtain 4.02 g (9.83 mmol) of a compound (I-1e) (yield: 25%).

The $^1$H-NMR of the obtained compound (I-1e) is shown below.

$^1$H-NMR (solvent: CDCl$_3$) δ (ppm): 0.9 (s, 3H), 1.0-1.1 (m, 6H), 1.3-1.5 (m, 4H), 1.5-1.6 (m, 1H), 1.6-1.8 (m, 8H), 1.9-2.1 (m, 4H), 2.2 (tt, 1H), 2.2 (tt, 1H), 4.0-4.2 (m, 2H), 4.2-4.3 (m, 2H), 5.8 (dd, 1H), 6.1 (dd, 1H), 6.4 (dd, 1H)

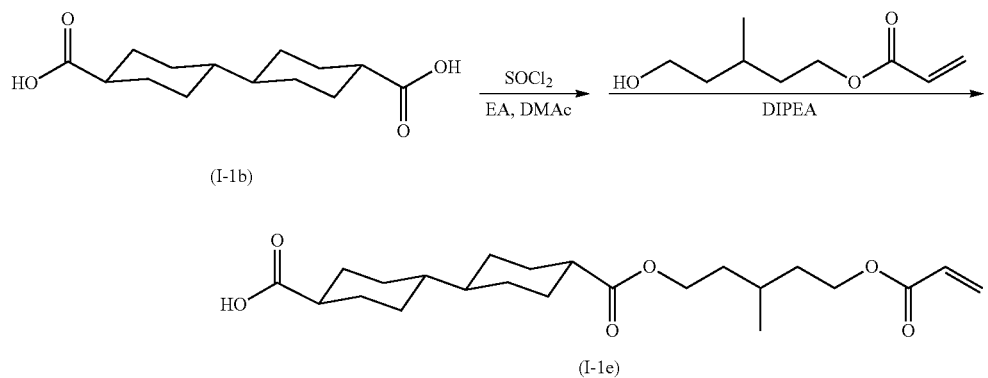

[Synthesis of Compound (I-1f)]

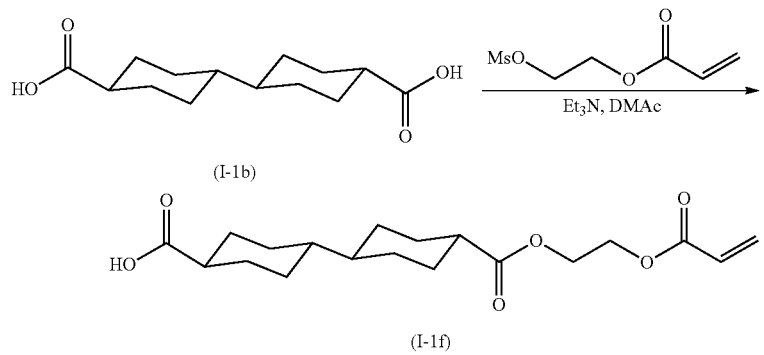

As shown in the scheme, 10.0 g (39.3 mmol) of the compound (I-1b), 30 ml of N,N-dimethylacetamide (DMAc), 10 ml of toluene, 7.96 g (78.6 mmol) of triethylamine, and 100 mg of 2,6-di-t-butyl-4-methylphenol were mixed at room temperature (23° C.).

8.40 g (43.2 mmol) of 2-methylsulfonyloxyethyl acrylate was added to the mixture, and the mixture was stirred at 90° C. for 5 hours. The mixture was cooled to room temperature, then a mixed solution of 2.60 g of concentrated hydrochloric acid and 20 ml of water was added thereto, and the mixture was stirred at 40° C. and then subjected to liquid separation.

Subsequently, 20 ml of toluene and 30 ml of a 5% aqueous sodium hydrogen carbonate solution were added to the organic layer, and the mixture was stirred at 40° C. and subjected to liquid separation.

Next, after washing the organic layer twice with 30 ml of a 1% aqueous sodium hydrogen carbonate solution, 20 mg of 2,2,6,6-tetramethylpiperidin-1-oxyl (TEMPO) was added thereto and then the solvent was evaporated under reduced pressure. Further purification was not performed and a solution of the compound (I-1f) in toluene was used in the next step as it was. As converted by means of NMR and high performance liquid chromatography (HPLC), the content and the yield of the main product were 28% and 45%, respectively.

[Synthesis of Compound (I-1 g)]

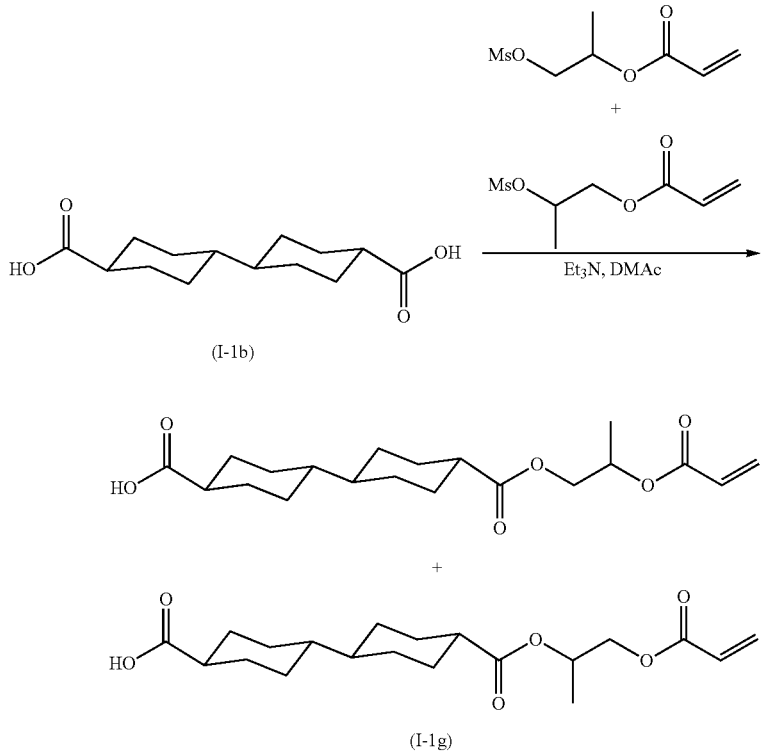

As shown in the scheme, a compound (I-1g) was synthesized in the same manner as for the compound (I-1f), except that a mixture of 2-methylsulfonyloxypropyl acrylate and 1-methylsulfonyloxypropyl acrylate was used instead of 2-methylsulfonyloxyethyl acrylate.

[Synthesis of Mixture (I-1 h)]

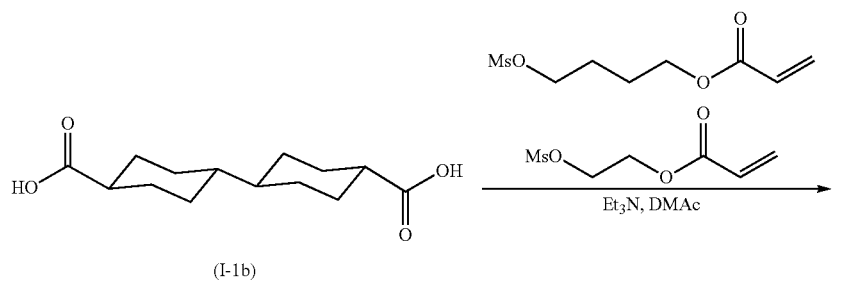

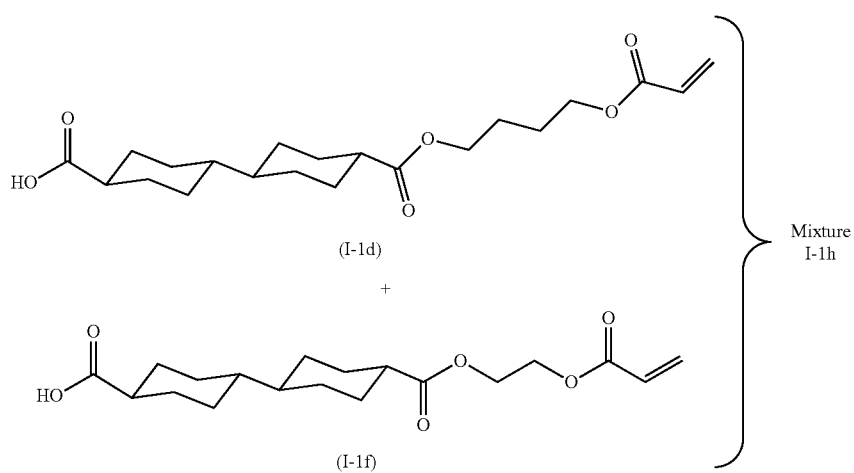

As shown in the scheme, a mixture (I-1h) was synthesized in the same manner as for the compound (I-1f), except that 4-methylsulfonyloxybutyl acrylate and 2-methylsulfonyloxyethyl acrylate were mixed and the mixture was used instead of 2-methylsulfonyloxyethyl acrylate. A molar ratio of 4-methylsulfonyloxybutyl acrylate to 2-methylsulfonyloxyethyl acrylate of 95:5 was used.

Example 1

[Synthesis of Compound (I-1-4)]

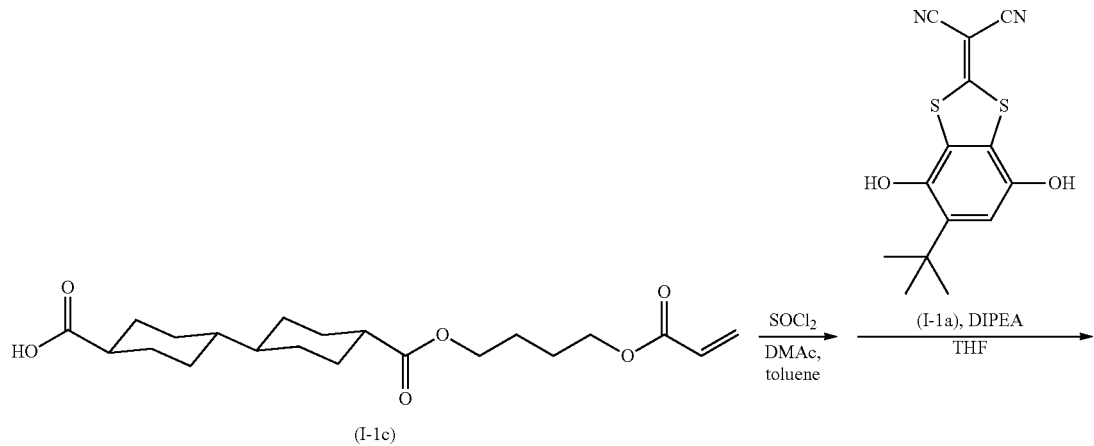

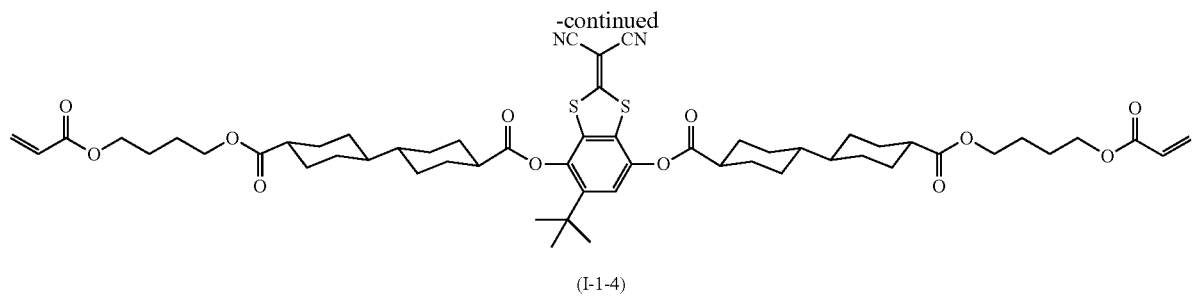

(I-1-4)

As shown in the scheme, 2.53 g (6.65 mmol) of the compound (I-1c), 15 ml of toluene, 4.5 ml of N,N-dimethylacetamide (DMAc), and 33 mg of 2,6-di-t-butyl-4-methylphenol were mixed at room temperature, and the internal temperature was lowered to 5° C. 0.58 ml (7.98 mmol) of thionyl chloride (SOCl$_2$) was added dropwise to the mixture while the internal temperature was maintained below 10° C. After stirring at 5° C. for 1 hour, a solution (5 ml) of 0.92 g (3.02 mmol) of the compound (I-1a) in tetrahydrofuran (THF) was added to the mixture. 2.90 ml (16.6 mmol) of N,N-diisopropylethylamine (DIPEA) was added dropwise thereto and the mixture was stirred at room temperature for 6 hours. After stirring, 15 ml of a 1 N aqueous hydrochloric acid solution and 15 ml of ethyl acetate were added thereto to stop the reaction, and the mixture was subjected to liquid separation. After the organic layer was washed with a 10%0/saline solution, 25 ml of isopropyl alcohol was added dropwise thereto at the internal temperature of 40° C., then the mixture was cooled to room temperature, and 15 ml of methanol was added dropwise thereto and the precipitated crystal was collected by filtration. After dissolving the obtained crude product in 10 ml of ethyl acetate, 35 ml of isopropyl alcohol was added dropwise thereto at the internal temperature of 40° C., then the mixture was cooled to room temperature, and 10 ml of methanol was added dropwise thereto and the precipitated crystal was collected by filtration. The obtained crude product was purified by silica gel column chromatography to obtain 2.65 g (2.58 mmol) of a compound (I-1-4) (yield: 85%).

The $^1$H-NMR of the obtained compound (I-1-4) is shown below.

$^1$H-NMR (solvent: CDCl$_3$) δ (ppm): 1.0-1.2 (m, 12H), 1.3 (s, 9H), 1.3-1.5 (m, 4H), 1.5-1.6 (m, 41), 1.7-1.8 (m, 8H), 1.8-2.0 (m, 8H), 2.0-2.1 (m, 4H), 2.1-2.3 (m, 6H), 2.5 (tt, 1H), 2.6 (tt, 1H), 4.1 (m, 4H), 4.2 (m, 4H), 5.8 (dd, 2H), 6.1 (dd, 2H), 6.4 (dd, 2H), 7.3 (s, 1H)

Example 2

[Synthesis of Compound (I-1-5)]

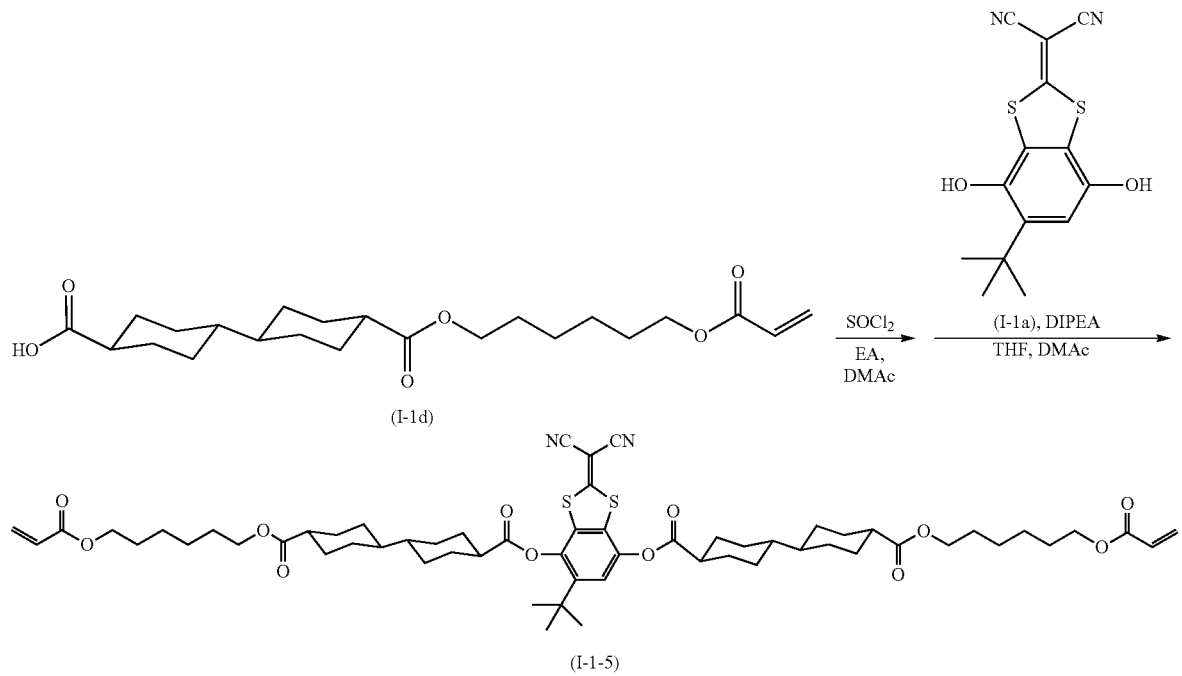

(I-1d)

(I-1-5)

As shown in the scheme, 5.0 g of a solution of the compound (I-1d) in toluene [the content of the compound (I-1d) was 1.03 g (2.53 mmol) as converted from NMR and HPLC], 5.0 ml of ethyl acetate (EA), 1.5 ml of N,N-dimethylacetamide (DMAc), and 13 mg of 2,6-di-t-butyl-4-methylphenol were mixed at room temperature, and the internal temperature was lowered to 5° C. 0.22 ml (3.04 mmol) of thionyl chloride (SOCl$_2$) was added dropwise to the mixture while the internal temperature was maintained below 10° C. After stirring at 5° C. for 1 hour, a solution (2 ml) of 0.35 g (1.15 mmol) of the compound (I-1a) in THF was added to the mixture. 1.10 ml (6.32 mmol) of N,N-diisopropylethylamine (DIPEA) was added dropwise thereto and the mixture was stirred at room temperature for 6 hours. After stirring, 5 ml of a 1 N aqueous hydrochloric acid solution and 5 ml of ethyl acetate were added thereto to stop the reaction, and the mixture was subjected to liquid separation. The organic layer was washed with a 10% saline solution and then dried over magnesium sulfate, and the solvent was evaporated under reduced pressure. The obtained crude product was purified by silica gel column chromatography to obtain 1.15 g (1.06 mmol) of a compound (I-1-5) (yield: 92%). The $^1$H-NMR of the obtained compound (I-1-5) is shown below.

$^1$H-NMR (solvent: CDCl$_3$) δ (ppm): 1.0-1.2 (m, 12H), 1.3 (s, 9H), 1.3-1.5 (m, 12H), 1.5-1.6 (m, 4H), 1.6-1.7 (m, 8H), 1.8-2.0 (m, 8H), 2.0-2.1 (m, 4H), 2.1-2.3 (m, 6H), 2.5 (tt, 1H), 2.6 (tt, 1H), 4.1 (t, 4H), 4.2 (t, 4H), 5.8 (dd, 2H), 6.1 (dd, 2H), 6.4 (dd, 2H), 7.3 (s, 1H)

Example 3

(Synthesis of Compound (I-1-6)

As shown in the scheme, 0.87 g (2.17 mmol) of the compound (I-1e), 4.5 ml of ethyl acetate (EA), 1.3 ml of N,N-dimethylacetamide (DMAc), and 11 mg of 2,6-di-t-butyl-4-methylphenol were mixed at room temperature, and the internal temperature was lowered to 5° C. 0.19 ml (2.60 mmol) of thionyl chloride (SOCl$_2$) was added dropwise to the mixture while the internal temperature was maintained below 10° C. After stirring at 5° C. for 1 hour, a solution (1.5 ml) of 0.30 g (0.70 mmol) of the compound (I-1a) in THF was added to the mixture. 0.94 ml (6.32 mmol) of N,N-diisopropylethylamine (DIPEA) was added dropwise thereto and the mixture was stirred at room temperature for 6 hours. After stirring, 5 ml of a 1 N aqueous hydrochloric acid solution and 5 ml of ethyl acetate were added thereto to stop the reaction, and the mixture was subjected to liquid separation. The organic layer was washed with a 10% saline solution and then dried over magnesium sulfate, and the solvent was evaporated under reduced pressure. The obtained crude product was purified by silica gel column chromatography to obtain 1.15 g (1.06 mmol) of a compound (I-1-6) (yield: 92%).

The $^1$H-NMR of the obtained compound (I-1-6) is shown below.

$^1$H-NMR (solvent: CDCl$_3$) δ (ppm): 1.0 (d, 6H), 1.0-1.2 (m, 12H), 1.3 (s, 9H), 1.3-1.5 (m, 4H), 1.5-1.6 (m, 6H), 1.7-1.8 (m, 8H), 1.8-1.9 (m, 4H), 1.9-2.0 (m, 4H), 2.0-2.1 (m, 4H), 2.2-2.3 (m, 6H), 2.5 (tt, 1H), 2.6 (tt, 1H), 4.1 (m, 4H), 4.2 (m, 4H), 5.8 (dd, 2H), 6.1 (dd, 2H), 6.4 (dd, 2H), 7.3 (s, 1H)

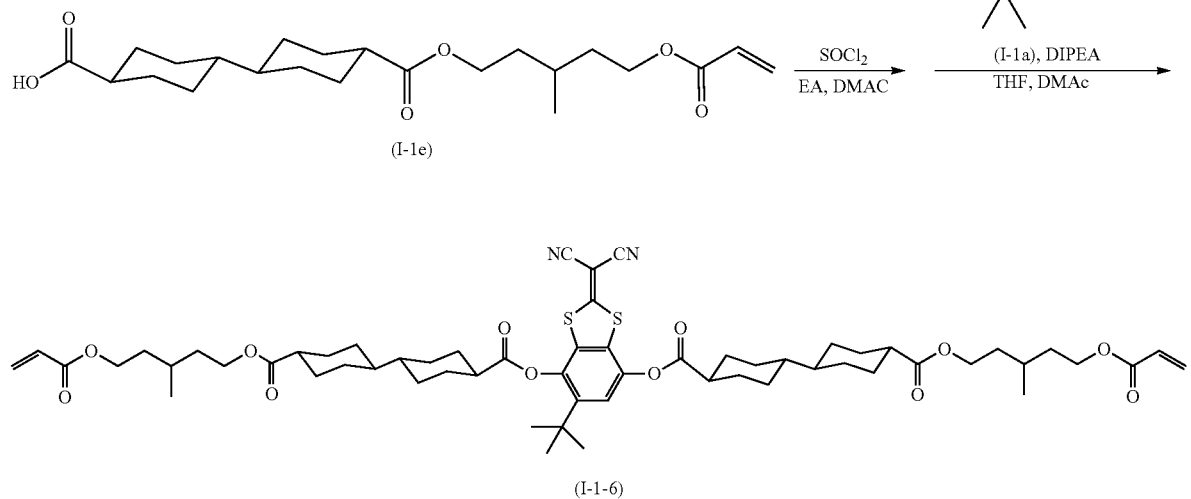

Example 4

[Synthesis of Compound (IV-1-4)]

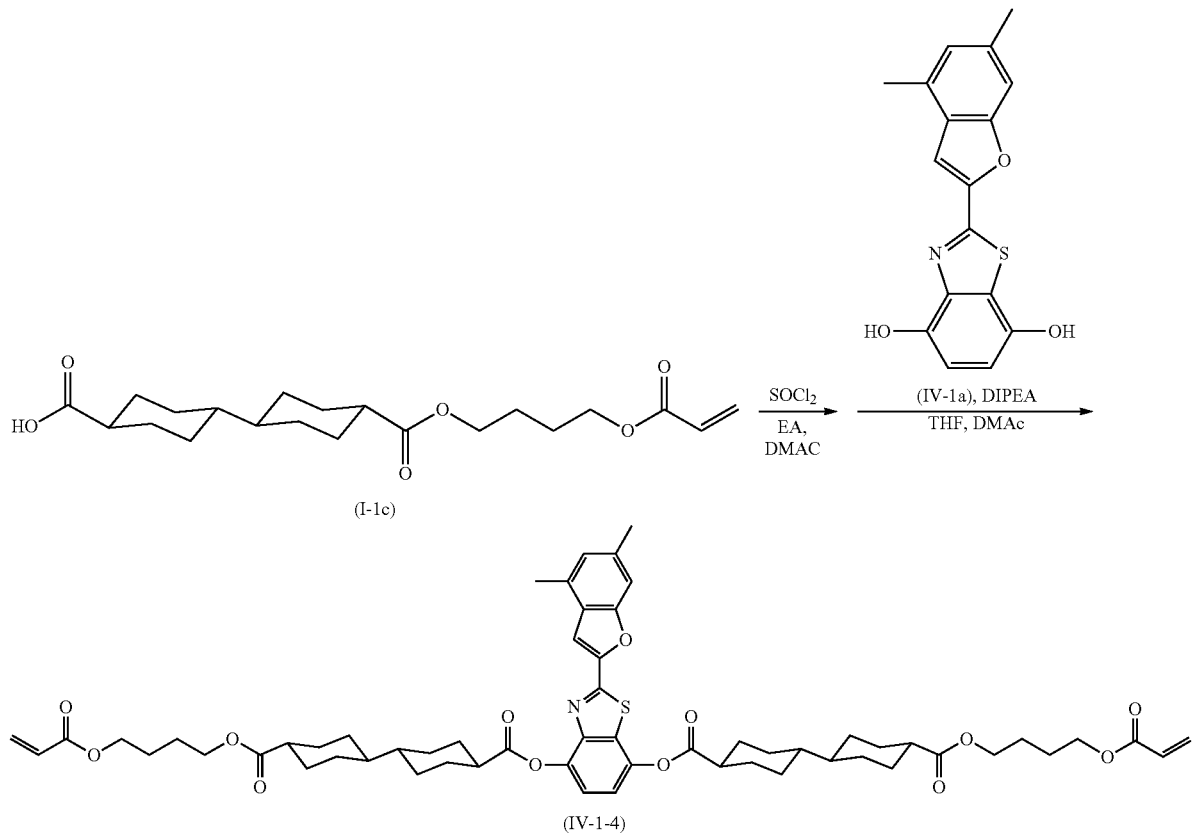

A compound (IV-1a) shown in the scheme was synthesized by the scheme described in paragraph 0463 of JP2011-207765A.

As shown in the scheme, 0.99 g (2.60 mmol) of the compound (I-1c), 5.0 ml of ethyl acetate (EA), 1.5 ml of N,N-dimethylacetamide (DMAc), and 13 mg of 2,6-di-t-butyl-4-methylphenol were mixed at room temperature, and the internal temperature was lowered to 5° C. 0.23 ml (3.12 mmol) of thionyl chloride (SOCl$_2$) was added dropwise to the mixture while the internal temperature was maintained below 10° C. After stirring at 5° C. for 1 hour, a solution (5.0 ml) of 0.31 g (1.18 mmol) of the compound (IV-1a) in THF was added to the mixture. 1.13 ml (6.50 mmol) of N,N-diisopropylethylamine (DIPEA) was added dropwise thereto and the mixture was stirred at room temperature for 2 hours. After stirring, 15 ml of a 1 N aqueous hydrochloric acid solution and 15 ml of ethyl acetate were added thereto to stop the reaction, and the mixture was subjected to liquid separation. The organic layer was washed with a 10% saline solution and then dried over magnesium sulfate, and the solvent was evaporated under reduced pressure. The obtained crude product was purified by silica gel column chromatography to obtain 0.99 g (0.956 mmol) of a compound (IV-1-4) (yield: 81%).

The $^1$H-NMR of the obtained compound (IV-1-4) is shown below.

$^1$H-NMR (solvent: CDCl$_3$) δ (ppm): 1.0-1.2 (m, 12H), 1.3-1.5 (m, 4H), 1.5-1.6 (m, 4H), 1.7-1.8 (m: 8H), 1.8-2.0 (m, 8H), 2.0-2.1 (m, 4H), 2.1-2.3 (m, 6H), 2.5 (s, 3H), 2.5 (s, 3H), 2.6 (tt, 1H), 2.7 (tt, 1H), 4.1 (m, 4H), 4.2 (m, 4H), 5.8 (m, 2H), 6.1 (m, 2H), 6.4 (m, 2H), 6.9 (brs, 1H), 7.2 (s, 2H), 7.5 (d, 1H)

Example 5

[Synthesis of Compound (II-1a)]

A compound (II-1a) represented by Formula (II-1a) was synthesized by the method described in paragraph 0169 (Example 15) of JP2016-081035A.

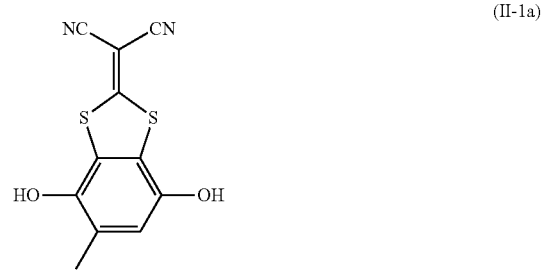 [SMILES: Cc1cc(O)c2c(c1O)SC(=C(C#N)C#N)S2]

[Synthesis of Mixture (R-1)]

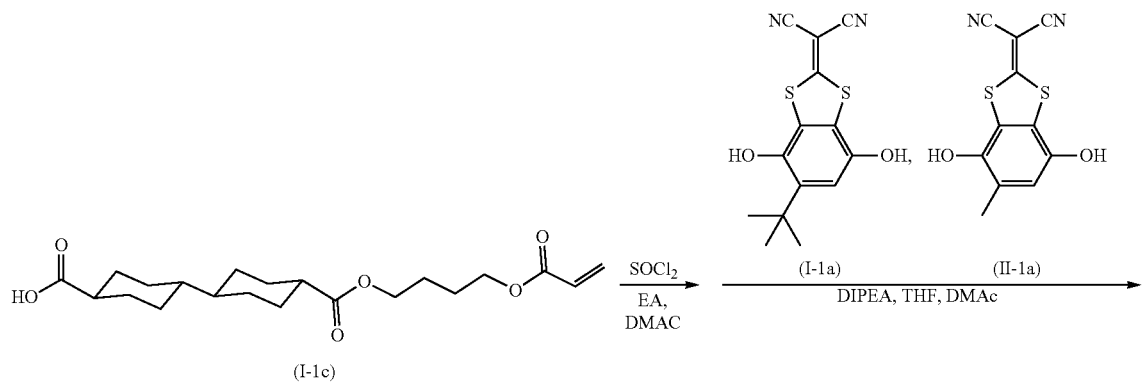

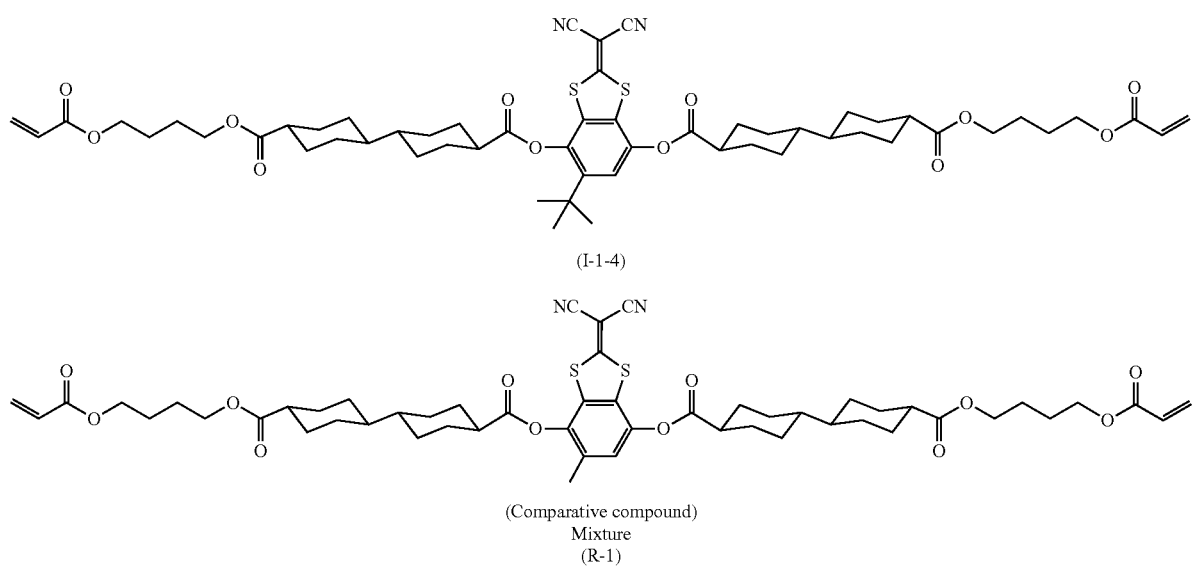

As shown in the scheme, 1.05 g (2.76 mmol) of the compound (I-1c), 6.0 ml of ethyl acetate (EA), 1.9 ml of N,N-dimethylacetamide (DMAc), and 14 mg of 2,6-di-t-butyl-4-methylphenol were mixed at room temperature, and the internal temperature was lowered to 5° C. 0.24 ml (3.31 mmol) of thionyl chloride (SOCl$_2$) was added dropwise to the mixture while the internal temperature was maintained below 10° C. After stirring at 5° C. for 1 hour, a solution (5.0 ml) of 286 mg (0.938 mmol) of the compound (I-1a) and 82.4 mg (0.314 mmol) of the compound (II-1a) in tetrahydrofuran (THF) was added to the mixture. 1.20 ml (6.89 mmol) of N,N-diisopropylethylamine (DIPEA) was added dropwise thereto and the mixture was stirred at room temperature for 6 hours. After stirring, 6 ml of a 1 N aqueous hydrochloric acid solution and 10 ml of ethyl acetate were added thereto to stop the reaction, and the mixture was subjected to liquid separation. The organic layer was washed with a 10% saline solution and then dried over magnesium sulfate, and the solvent was evaporated under reduced pressure. The obtained crude product was purified by silica gel column chromatography to obtain 1.16 g of a mixture (R-1) of the compound (I-1-4) and a comparative compound. From the analysis by $^1$H-NMR, the composition of the mixture was 72% by mass of the compound (I-1-4) and 28% by mass of the comparative compound.

Example 6

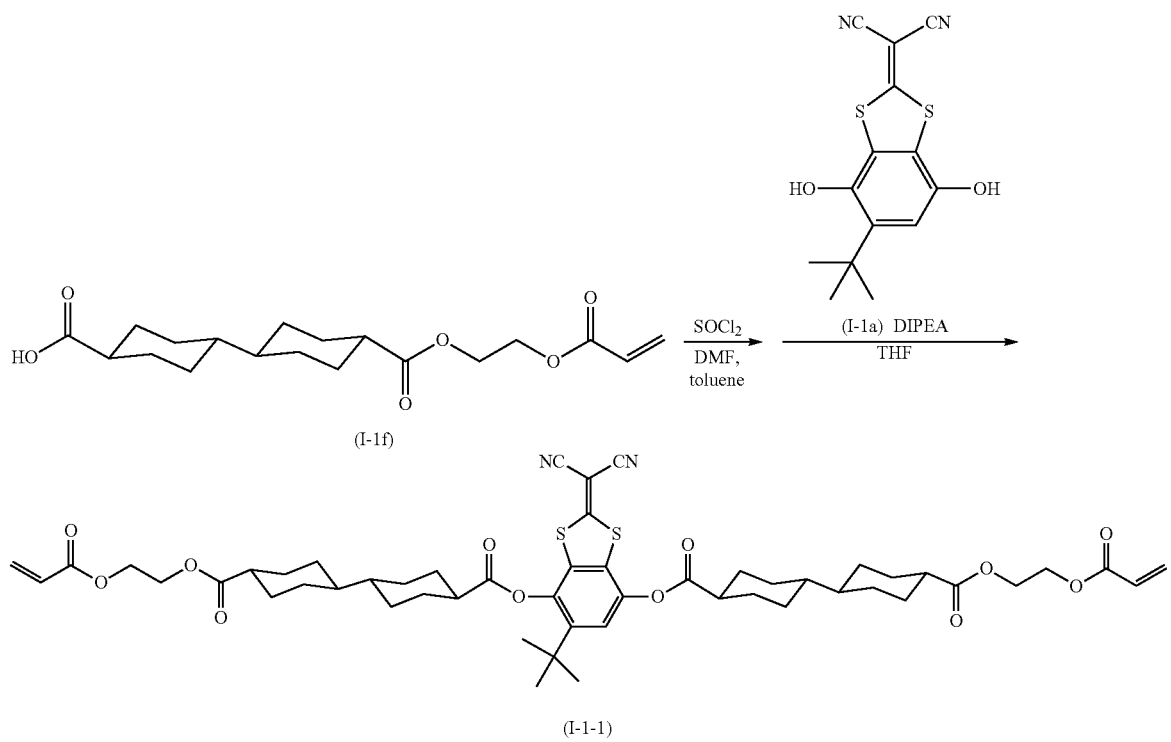

As shown in the scheme, 45 g of a solution of the compound (I-1f) in toluene [the content of the compound (I-1f) was 11.90 g (33.9 mmol) as converted from NMR and HPLC], 2.82 g of N,N-dimethylformamide (DMF), and 15 mg of 2,6-di-t-butyl-4-methylphenol were mixed at room temperature, and the internal temperature was lowered to 5° C. 4.47 g (37.6 mmol) of thionyl chloride (SOCl$_2$) was added dropwise to the mixture while the internal temperature was maintained below 10° C. After stirring at 20° C. for 30 minutes, the separated lower layer was removed. Next, the internal temperature was cooled to 5° C., a mixed solution of 4.69 g (15.4 mmol) of the compound (I-1a), a solution (20 ml) of ethyl acetate, and N-ethylpyrrolidone (6 ml) was added thereto, 5.57 g (43.2 mmol) of N,N-diisopropylethylamine (DIPEA) was further added dropwise thereto while the internal temperature was maintained below 10° C., and then the mixture was stirred at room temperature at 30° C. for 2 hours. After stirring, 15 ml of methanol was added thereto to stop the reaction, and then the temperature of the mixture was raised to 45° C. Thereafter, 25 ml of water was added dropwise thereto, and then the mixture was neutralized by addition of 0.78 g of triethylamine. The aqueous layer was subjected to liquid separation, 15 ml of ethyl acetate and 100 ml of methanol were added to the organic layer, followed by cooling to 5° C. to cause precipitation of crystals, and then the precipitated crystals were collected by filtration. As a result, 12.7 g (13.1 mmol) of the compound represented by Formula (I-1-1) was obtained (yield: 85%).

The obtained compound was identified by $^1$H-NMR and MS.

(I-1-1) MS (m/z)=973 ([M+H]+)

Example 7

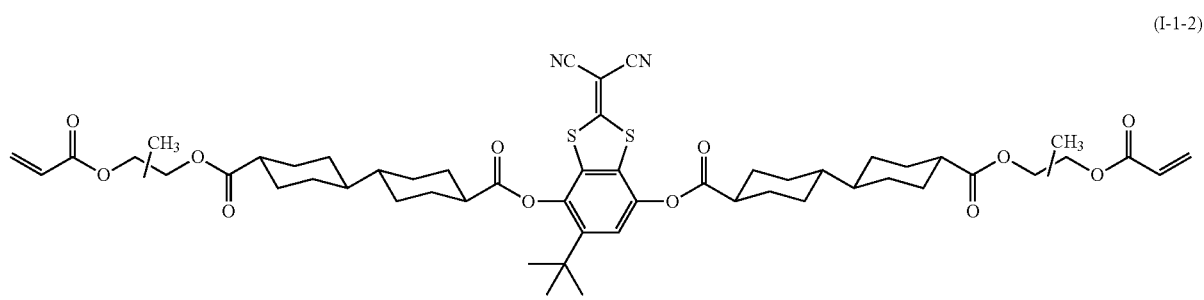

A compound (I-1-2) was synthesized in the same manner as for the synthesis of the compound (I-1-1), except that the compound (I-1g) was used instead of the compound (I-1f).

The obtained compound was identified by $^1$H-NMR and MS.

(I-1-2) MS (m/z)=1001 ([M+H]+)

Example 8

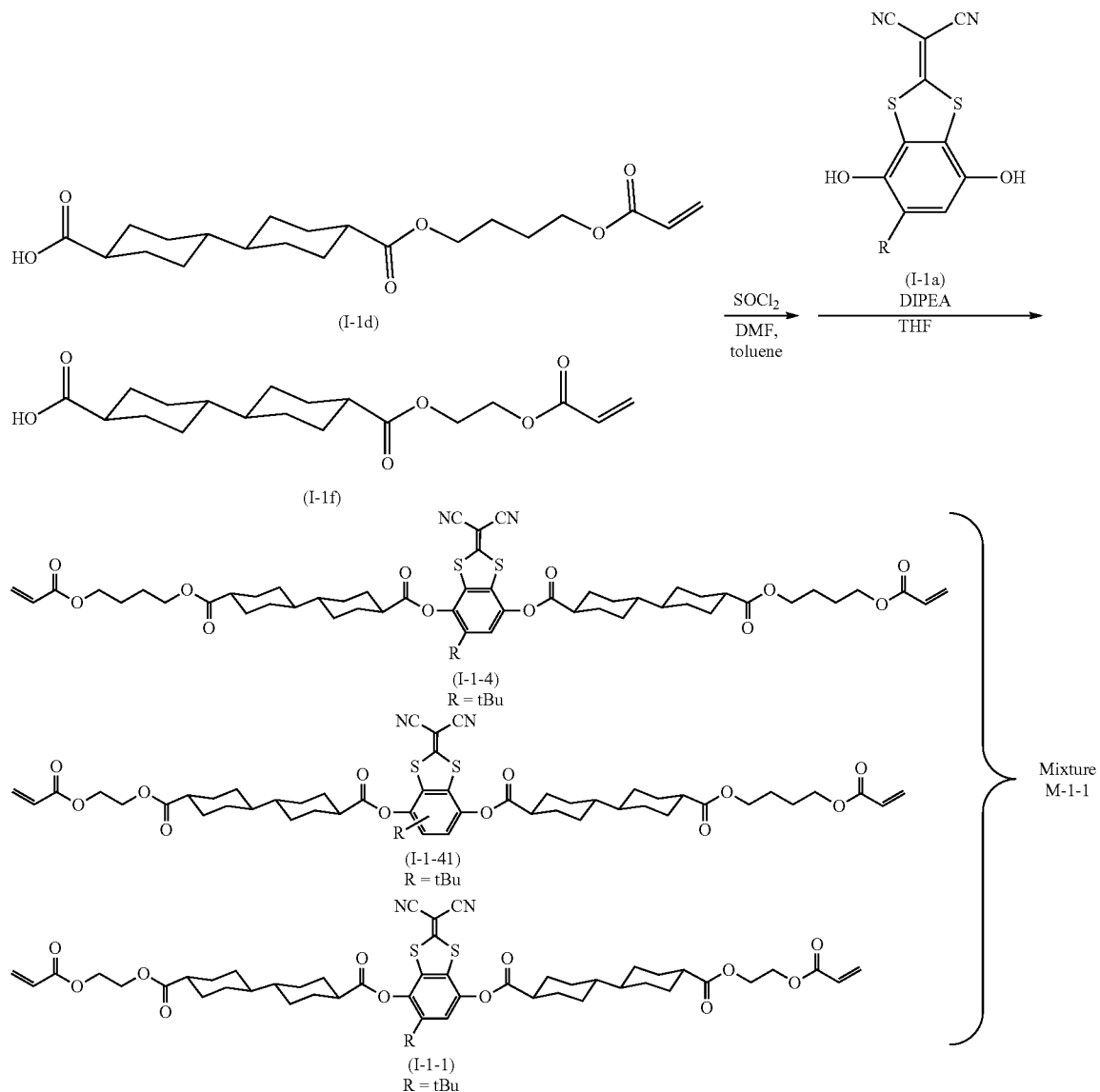

As shown in the scheme, 6.70 g (17.6 mmol) of the compound (I-1d), 1.55 g (4.4 mmol) of the compound (I-1f), 2.00 g of N,N-dimethylformamide (DMF), 25 ml of toluene, and 20 mg of 2,6-di-t-butyl-4-methylphenol were mixed at room temperature, and the internal temperature was lowered to 5° C. 2.80 g (23.5 mmol) of thionyl chloride (SOCl$_2$) was added dropwise to the mixture while the internal temperature was maintained below 10° C. After stirring at 20° C. for 30 minutes, the separated lower layer was removed. Next, the internal temperature was cooled to 5° C., and a mixed solution of 3.04 g (10.0 mmol) of the compound (I-1a), a solution (20 ml) of ethyl acetate, and N-ethylpyrrolidone (6 ml) were added thereto. 3.49 g (27.0 mmol) of N,N-diisopropylethylamine (DIPEA) was added dropwise to the mixture while the internal temperature was maintained below 10° C., and then the mixture was stirred at 30° C. for 2 hours. After stirring, 10 ml of methanol was added thereto to stop the reaction, and then the temperature of the mixture was raised to 45° C. Thereafter, 20 ml of water was added dropwise thereto, and then the mixture was neutralized by addition of 0.51 g of triethylamine. The aqueous layer was subjected to liquid separation, 10 ml of ethyl acetate and 70 ml of methanol were added to the organic layer, followed by cooling to 5° C. to cause precipitation of crystals, and then the precipitated crystals were collected by filtration. As a result, 8.27 g of (M-1-1) which is a mixture of Formulae (I-1-4), (I-1-41), and (I-1-1) was obtained (yield: 85%). As a result of the measurement by HPLC, the ratio of (I-1-4)/(I-1-41)/(I-1-1) was 65/31/4.

Example 9

A mixture (M-1-2) was synthesized using a mixture (I-1h) instead of the compound (I-1d) and the compound (I-1t). As a result of the measurement with HPLC, the ratio of (I-1-4)/(I-1-41)/(I-1-1) was 90/10/0.1.

Example 10

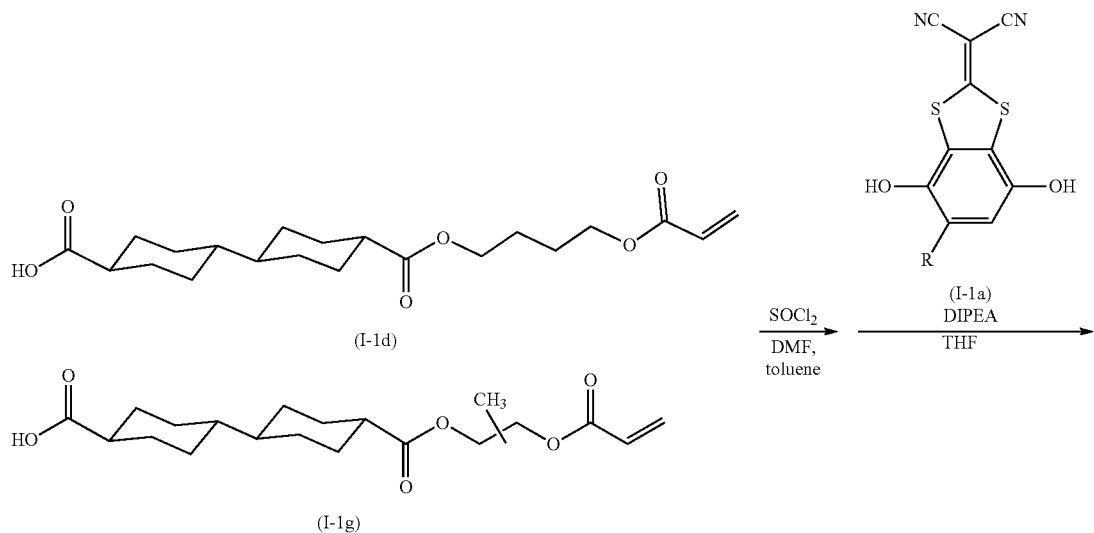

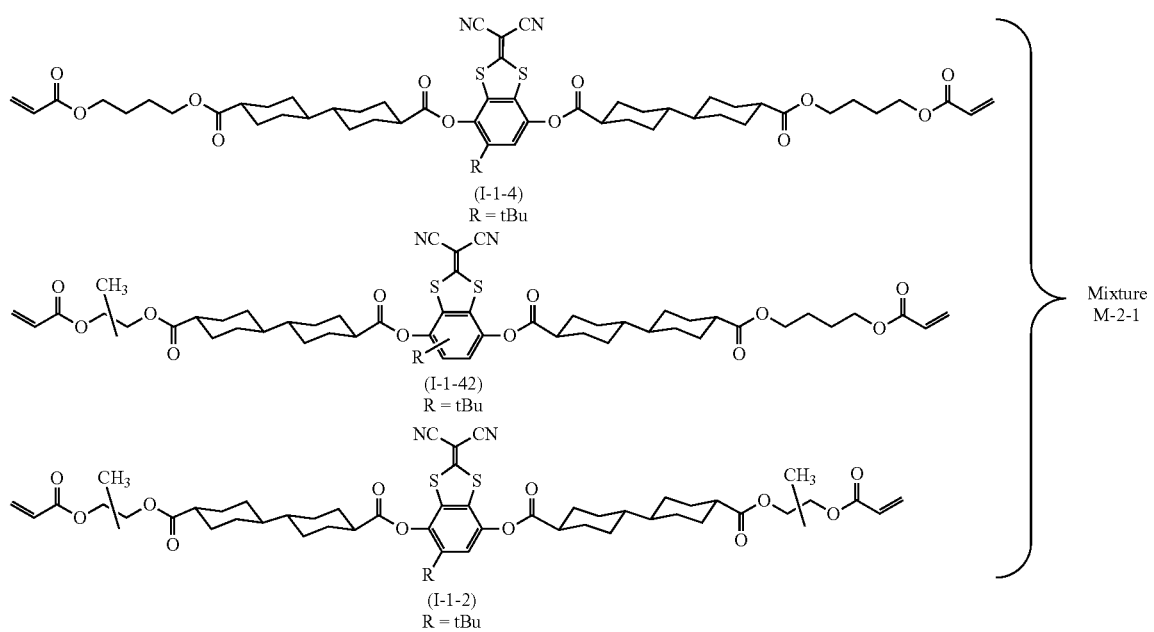

As shown in the scheme, a mixture (M-2-1) was synthesized in the same manner as for the mixture (M-1-1), except that a compound (I-1g) was used instead of the compound (I-1d) and the introduction proportion of the compound (I-1f) and the compound (I-1g) was set to 95:5. As a result of the measurement with HPLC, the ratio of (I-1-4)/(I-1-42)/(I-1-2) was 91/9/0.1.

Comparative Example 1

A compound B of the following formula in which n is 1 was synthesized by the method described in paragraphs 0161 to 0163 of JP2010-084032A.

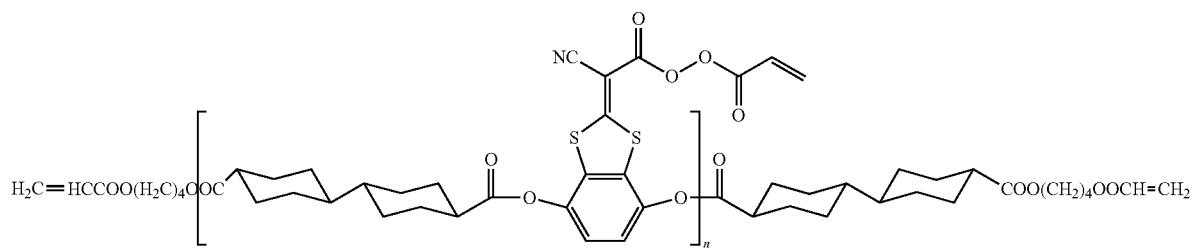
Comparative Example 2
A compound (I-4) represented by Formula (I-4) was synthesized by the method described in paragraph 0122 (Example 4) of JP2016-081035A.
(I-4)
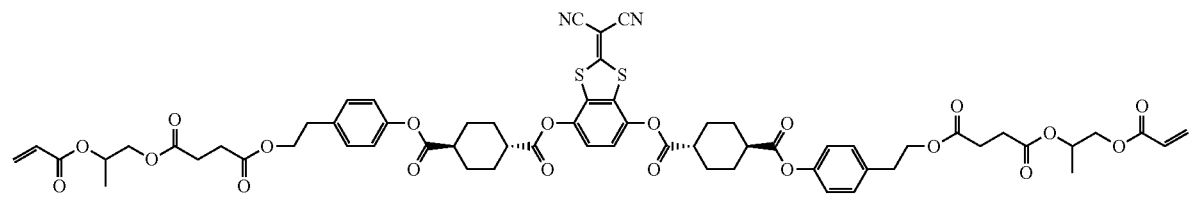
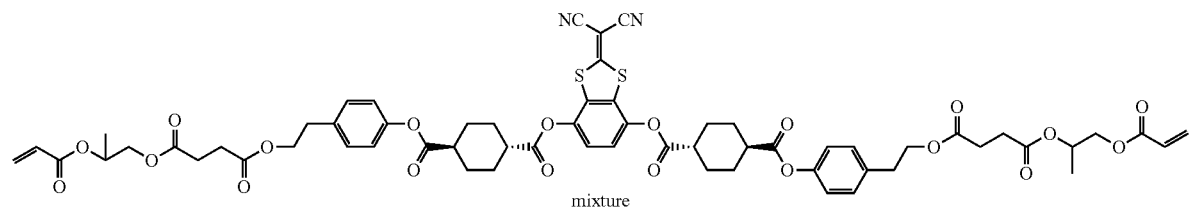
Comparative Example 3
A compound (A11-1) represented by Formula (A11-1) was synthesized by the method described in paragraph 0252 of JP2011-207765A.
(A11-1)
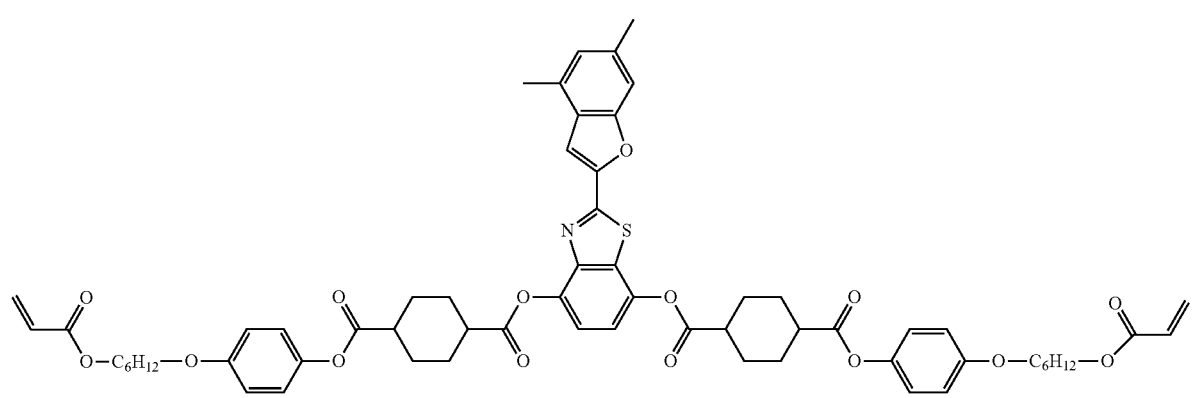

<Clog P Value>
With regard to the polymerizable liquid crystal compounds synthesized in Examples 1 to 5 and Comparative Examples 1 to 3, a Clog P value of Ar corresponding to the reciprocal wavelength dispersion expressing portion was calculated by the above-mentioned method. The results are shown in Table 3 below.

<Phase Transition Temperature>
With regard to the polymerizable liquid crystal compounds synthesized in Examples 1 to 5 and Comparative Examples 1 to 3, a phase transition temperature was measured using a polarization microscope. The results are shown in Table 3 below.

Here, in Table 3 below, "C 143 N 208 I" in Example 1 indicates that the phase transition temperature from the crystal state to the nematic phase is 143° C. and the phase transition temperature from the nematic phase to the isotropic liquid is 208° C.; "C 109 Sm 133 N 154 I" in Comparative Example 2 indicates that the phase transition temperature from the crystal state to the smectic phase is 109° C., the phase transition temperature from the smectic phase to the nematic phase is 133° C., and the phase transition temperature from the nematic phase to the isotropic liquid is 154° C.; and "C 153 N>200 I" in Comparative Example 3 indicates that the phase transition temperature from the crystal state to the nematic phase is 153° C. and the nematic phase is shown at 200° C. or higher but polymerization is developed at the same time, which makes it difficult to measure the phase transition temperature from the nematic phase to the isotropic liquid.

[Manufacture of Optical Film]
A polymerizable composition (coating liquid for an optically anisotropic film) having the following composition was prepared and applied onto a glass substrate including a rubbing-treated polyimide alignment film (SE-150 manufactured by Nissan Chemical Industries, Ltd.) by spin coating. The coating film was subjected to an alignment treatment at a temperature shown in Table 3 below to form a liquid crystal layer. Thereafter, the liquid crystal layer was cooled to a temperature during exposure described in Table 3 below and subjected to alignment fixation by irradiation with ultraviolet rays at 1,000 mJ/cm$^2$ to form an optically anisotropic film, whereby an optical film for measuring a wavelength dispersion was obtained. With regard to Example 5, as a polymerizable liquid crystal compound, the above-mentioned mixture (R-1), that is, a mixture containing 72% by mass of the compound (I-1-4) shown in Table 3 below and 28% by mass of the comparative compound was used.

| Coating liquid for optically anisotropic layer film | |
|---|---|
| Polymerizable liquid crystal compound (the compound described in Table 3 below) | 15.00 parts by mass |
| Photopolymerization initiator (IRGACURE 819, manufactured by BASF) | 0.45 parts by mass |
| The following fluorine-containing compound A | 0.12 parts by mass |
| Chloroform | 35.00 parts by mass |

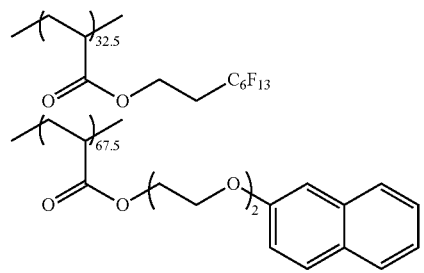

Fluorine-containing compound A

<Retardation>
With regard to the manufactured optical film, a retardation value at a wavelength of 450 nm (Re(450)) and a retardation value at a wavelength of 550 nm (Re(550)) were measured using AxoScan (OPMF-1, manufactured by Opto Science, Inc.), and Re(450)/Re(550) was calculated. The results are shown in Table 3 below.

<Moisture-Heat Resistance>
With regard to a test condition for moisture-heat resistance, a test in which the film was left to stand for 500 hours in an environment of a relative humidity of 85% at 85° C. was performed. Re(550) of the optical film after the test was measured and the moisture-heat resistance was evaluated in accordance with the following standard. The results are shown in Table 3 below.

A: A variation in Re(550) after the test with respect to the initial phase difference value is less than 10% of the initial value.

B: A variation in Re(550) after the test with respect to the initial phase difference value is 10% or more and less than 30% of the initial value.

C: A variation in Re(550) after the test with respect to the initial phase difference value is 30% or more of the initial value.

<Light Resistance>
With regard to the manufactured optical film, a glass substrate was set in a Xenon irradiator (SX75 manufactured by Suga Test Instruments Co., Ltd.) such that the coating film of the polymerizable liquid crystal composition served as a surface to be irradiated, and a test was performed by irradiation with light for 200 hours using a #275 filter. Re(550) of the optical film after the test was measured and the light resistance was evaluated in accordance with the following standard. The results are shown in Table 3 below.

A: A variation in Re(550) after the test with respect to the initial phase difference value is less than 5% of the initial value.

B: A variation in Re(550) after the test with respect to the initial phase difference value is 5% or more and less than 15% of the initial value.

C: A variation in Re(550) after the test with respect to the initial phase difference value is 15% or more of the initial value.

TABLE 3

| | Polymerizable liquid crystal compound | Ar Clog P value | Phase transition temperature | Alignment treatment temperature (° C.) | Temperature (° C.) during exposure | Re(450) | Re(550) | Re(450)/ Re(550) | Moisture-heat resistance | Light resistance |
|---|---|---|---|---|---|---|---|---|---|---|
| Example 1 | Compound (I-1-4) | 4.44 | C 143 N208 I | 200 | 135 | 62 | 90 | 0.69 | A | A |
| Example 2 | Compound (I-1-5) | 4.44 | C 120N 158 I | 131 | 130 | 56 | 78 | 0.72 | A | A |
| Example 3 | Compound (I-1-6) | 4.44 | C 90 N 122 I | 104 | 100 | 53 | 73 | 0.72 | A | A |

TABLE 3-continued

| | Polymerizable liquid crystal compound | Ar Clog P value | Phase transition temperature | Alignment treatment temperature (° C.) | Temperature (° C.) during exposure | Re(450) | Re(550) | Re(450)/ Re(550) | Moisture-heat resistance | Light resistance |
|---|---|---|---|---|---|---|---|---|---|---|
| Example 4 | Compound (IV-1-4) | 5.95 | C 155 N 240 I | 200 | 135 | 47 | 70 | 0.67 | A | C |
| Example 5 | Compound (I-1-4) Comparative compound | 4.44 3.12 | C 136 N220 I | 200 | 135 | 71 | 108 | 0.66 | A | A |
| Comparative Example 1 | Compound B | 3.68 | C 96 N 192 I | 180 | 140 | 60 | 81 | 0.74 | B | B |
| Comparative Example 2 | Compound (I-4) | 2.62 | C 109 Sm 133 N 154 I | 140 | 120 | 131 | 160 | 0.82 | C | A |
| Comparative Example 3 | Compound (A11-1) | 5.95 | C 153 N > 200 I | 180 | 140 | 112 | 138 | 0.81 | A | C |

From the results shown in Table 3, it could be seen that in a case where the Clog P value of the reciprocal wavelength dispersion expressing portion (Ar) of the polymerizable liquid crystal compound is within the range of 4.3 or more and less than 7.0, the moisture-heat resistance of an optically anisotropic film formed is deteriorated (Comparative Examples 1 and 2).

In addition, it could be seen that even in a case where the Clog P value of the reciprocal wavelength dispersion expressing portion (Ar) of the polymerizable liquid crystal compound is within the range of 4.3 or more and less than 7.0 and a skeleton having cyclohexane rings linked to each other via a single bond is not included in the major axis direction, the reciprocal wavelength dispersion of an optically anisotropic film formed was deteriorated (Comparative Example 3).

In contrast, it could be seen that with a polymerizable liquid crystal compound which has a Clog P value of the reciprocal wavelength dispersion expressing portion (Ar) within the range of 4.3 or more and less than 7.0 and a skeleton having cyclohexane rings linked to each other via a single bond in the major axis direction of a molecule having a reciprocal wavelength dispersion expressing portion at the center, the reciprocal wavelength dispersion and the moisture-heat resistance of an optically anisotropic film formed is improved (Examples 1 to 5).

<Manufacture of Optical Film>

A polymerizable composition (coating liquid for an optically anisotropic film) having the following composition was prepared and applied onto a glass substrate including a rubbing-treated polyimide alignment film (SE-150 manufactured by Nissan Chemical Industries, Ltd.) by spin coating. In the same manner as in Examples 1 to 5, an alignment treatment and alignment fixation were performed to form an optically anisotropic film and thus, form an optical film for measuring a wavelength dispersion. Evaluations of the retardation and the light resistance were carried out under the same conditions as in Examples 1 to 5.

| Coating liquid for optically anisotropic film | |
|---|---|
| Polymerizable liquid crystal compound (compound described in Table 4 below) | 15 parts by mass |
| Photopolymerization initiator (IRGACURE 819, manufactured by BASF) | 0.45 parts by mass |
| The fluorine-containing compound A | 0.12 parts by mass |
| Cyclopentanone | 35 parts by mass |

TABLE 4

| | Polymerizable liquid crystal compound | Ar Clog P value | Re(450) | Re(550) | Re(450)/ Re(550) | Moisture-heat resistance | Light resistance |
|---|---|---|---|---|---|---|---|
| Example 6 | Compound (I-1-1) | 4.44 | 63 | 92 | 0.69 | A | A |
| Example 7 | Compound (I-1-2) | 4.44 | 59 | 82 | 0.72 | A | A |
| Example 8 | Mixture (M-1-1) | 4.44 | 67 | 95 | 0.71 | A | A |
| Example 9 | Mixture (M-1-2) | 4.44 | 67 | 93 | 0.72 | A | A |
| Example 10 | Mixture (M-2-1) | 4.44 | 65 | 91 | 0.71 | A | A |
| Example 11 | Compound (I-1-2) Compound (I-1-4) | 4.44 | 60 | 84 | 0.72 | A | A |

From the results shown in Table 4, it could be seen that in a case where the Clog P value of the reciprocal wavelength dispersion expressing portion (Ar) of the polymerizable liquid crystal compound is 4.3 or more and less than 7.0, the reciprocal wavelength dispersion, the moisture-heat resistance, and the light resistance of an optically anisotropic film formed are excellent.

<Synthesis of Polymer PA-1 Having Photo-Aligned Group>

According to the method described in Langmuir, 32(36), 9245-9253 (2016), a monomer m-1 shown below was synthesized using 2-hydroxyethylmethacrylate (HEMA) (reagent from Tokyo Chemical Industry Co., Ltd.) and the following cinnamic acid chloride derivative.

Cinnamic Acid Chloride Derivative

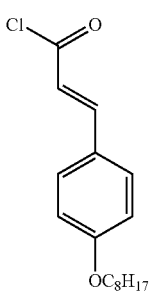

Monomer m-1

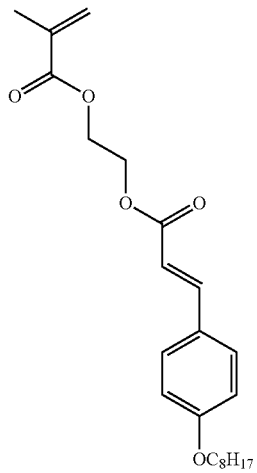

5 parts by mass of 2-butanone was introduced as a solvent into a flask equipped with a cooling pipe, a thermometer, and a stirrer, nitrogen flowed into the flask at 5 ml/min, and the flask was refluxed under heating in a water bath. A solution obtained by mixing 5 parts by mass of the monomer m-1, 5 parts by mass of CYCLOMER M100 (manufactured by Daicel Chemical Industries, Ltd.), 1 part by mass of 2,2'-azobis(isobutyronitrile) as a polymerization initiator, and 5 parts by mass of 2-butanone as a solvent was added dropwise thereto for 3 hours, and the mixture was further stirred for 3 hours while keeping the refluxing state. After completion of the reaction, the mixture was left to be cooled to room temperature and diluted by addition of 30 parts by mass of 2-butanone to obtain approximately 20% by mass of polymer solution. The obtained polymer solution was put into methanol in a large excess to settle a polymer, and the recovered sediment was separated by filtration and washed with a large amount of methanol, and then dried with blast drying at 50° C. for 12 hours to obtain a polymer PA-1 having a photo-aligned group.

Polymer PA-1

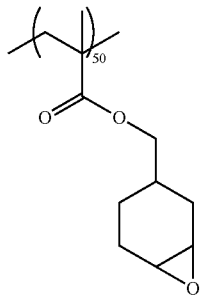

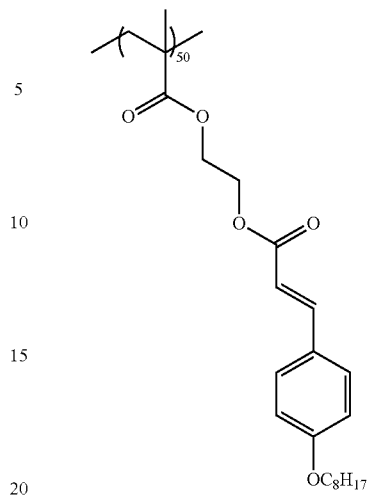

<Manufacture of Alignment Film P-3>

The following coating liquid forming an alignment film P-3 was continuously applied onto a commercially available triacetyl cellulose film "Z-TAC" (manufactured by FUJIFILM Corporation) with a #2.4 wire bar. A support having the coating film formed thereon was dried with hot air at 140° C. for 120 seconds, and subsequently irradiated with polarized ultraviolet rays (10 mJ/cm$^2$, using an ultra-high-pressure mercury lamp) to form an alignment film P-3.

| Coaxing liquid for forming alignment film P-3 | |
|---|---|
| The polymer PA-1 | 100.00 parts by mass |
| Isopropyl alcohol | 16.50 parts by mass |
| Butyl acetate | 1072.00 parts by mass |
| Methyl ethyl ketone | 268.00 parts by mass |

<Formation of Positive A-Plate A-1>

The following composition A-1 was applied onto the alignment film P-3 provided on the triacetyl cellulose film using a bar coater. After the coating film formed on the alignment film P-3 was heated with hot air at 135° C. and then cooled to 60° C., the coating film was irradiated with ultraviolet rays at 100 mJ/cm$^2$ at a wavelength of 365 nm under a nitrogen atmosphere using a high-pressure mercury lamp, and subsequently irradiated with ultraviolet rays at 500 mJ/cm$^2$ under heating at 120° C. to fix the alignment of the liquid crystal compound, thereby manufacturing a film A-1 including a positive A-plate A-1. Re(550) was 144 nm.

| Composition A-1 | |
|---|---|
| The compound (I-1-4) | 84.00 parts by mass |
| The following polymerizable liquid crystal compound L-3 | 16.00 parts by mass |
| The following polymerization initiator PI-1 | 0.50 parts by mass |
| The following leveling agent T-1 | 0.20 parts by mass |
| Chloroform | 570.00 parts by mass |

Polymerizable liquid crystal compound L-3

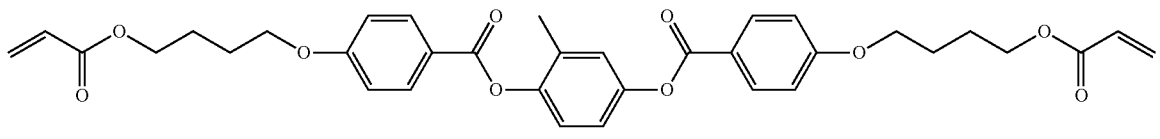 [SMILES: C=CC(=O)OCCCCOc1ccc(C(=O)Oc2ccc(OC(=O)c3ccc(OCCCCOC(=O)C=C)cc3)c(C)c2)cc1]

Polymerization initiator PI-1

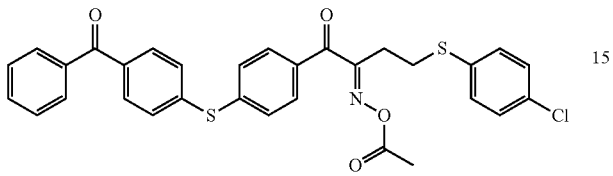

Leveling agent T-1

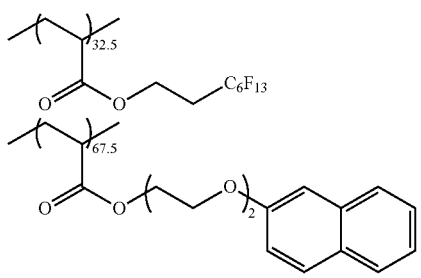

<Formation of Positive A-Plate A-2>

A positive A-plate A-2 was manufactured in the same manner as for the positive A-plate A-1, except that the following composition A-2 was used instead of the composition A-1.

| Composition A-2 | |
|---|---|
| The mixture (R-1) | 73.00 parts by mass |
| The polymerizable liquid crystal compound L-3 | 27.00 parts by mass |
| The polymerization initiator PI-1 | 0.50 parts by mass |
| The leveling agent T-1 | 0.20 parts by mass |
| Chloroform | 570.00 parts by mass |

<Formation of Positive A-Plate A-5>

A positive A-plate A-5 was manufactured in the same manner as for the positive A-plate A-1, except that the following composition A-5 was used instead of the composition A-1.

| Composition A-5 | |
|---|---|
| The compound (I-1-4) | 80.00 parts by mass |
| The polymerizable liquid crystal compound L-3 | 20.00 parts by mass |
| The polymerization initiator PI-1 | 0.50 parts by mass |
| The leveling agent T-1 | 0.20 parts by mass |
| The compound UV-1 | 5.00 parts by mass |
| Chloroform | 570.00 parts by mass |

Compound UV-1

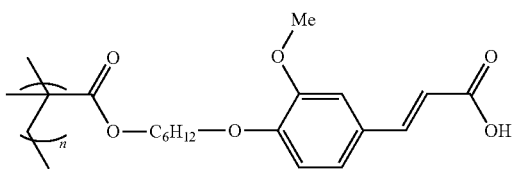

<Formation of Positive C-Plate C-1>

A film C-1 having a positive C-plate C-1 on a temporary support for forming a C-plate was manufactured by the same method as for the positive C-plate described in paragraph 0124 of JP2015-200861A. Rth(550) was set to −69 nm by adjusting the film thickness.

<Manufacture of Alignment Film P-4>

A cycloolefin polymer (COP) film (ZF-14, manufactured by ZEON Corporation) was treated once under conditions of an output of 0.3 kW and a treating speed of 3 m/min using a corona treatment apparatus (AGF-B10, manufactured by Kasuga Electric Works Ltd.). The following composition was applied onto the corona-treated surface with a bar coater, dried at 80° C. for 1 minute, and subjected to polarization UV exposure at an accumulated light amount of 100 mJ/cm² using a polarized UV irradiation apparatus (SPOT CURE SP-7; manufactured by Ushio Inc.). The film thickness of the obtained alignment film was measured with a laser microscope (LEXT, manufactured by Olympus Corporation) and found to be 100 nm.

| Coating liquid for forming alignment film P-4 | |
|---|---|
| The following polymer PA-10 | 5.0 parts by mass |
| Cyclopentanone | 95.0 parts by mass |

Polymer PA-10

<Formation of Positive A-Plate A-3>

A film A-3 including a positive A-plate A-3 was manufactured in the same manner as for the positive A-plate A-1, except that an alignment film P-4 provided on the cycloolefin polymer film was used instead of the alignment film P-3 provided on the triacetyl cellulose film. Re(550) was 144 nm.

<Formation of Polarizing Plate>

A surface of a TD80UL (manufactured by FUJIFILM Corporation) which is a support was subjected to an alkali saponification treatment. Specifically, the support was immersed in a 1.5 N aqueous sodium hydroxide solution at 55° C. for 2 minutes, and the extracted support was washed in a water-washing bathtub at room temperature and neutralized with a 0.1 N sulfuric acid at 30° C. Thereafter, the obtained support was washed again in the water-washing bathtub at room temperature and further dried with a hot air at 100° C. Subsequently, a roll-shaped polyvinyl alcohol film having a thickness of 80 μm was continuously stretched five times in an iodine aqueous solution, and the stretched film was dried to obtain a polarizer having a thickness of 20 μm.

The obtained polarizer and the support (TD80UL) which had been subjected to an alkali saponification treatment were stuck, and then Z-TAC (manufactured by FUJIFILM Corporation) was stuck onto the other surface to obtain a polarizing plate 0 in which both surfaces of the polarizer were held by films.

Next, the polarizer of the polarizing plate 0 and the support surface of the positive A-plate were bonded using a pressure-sensitive adhesive in such a relationship that the slow axis of each of the manufactured positive A-plates A-1 to A-3 and the absorption axis of the polarizer were arranged as shown in Table 5, subsequently, the support of the positive A-plate was peeled off, and thus, only the positive A-plate was transferred onto the polarizing plate. Subsequently, the coating surface of the positive C-plate C-1 was stuck onto the surface of the transferred positive A-plate using the pressure-sensitive adhesive, the temporary support for forming a film C-1 was peeled off, and thus, only the positive C-plate C-1 was transferred onto the positive A-plate A, thereby manufacturing polarizing plates 1 to 6.

TABLE 5

| | Positive A-plate | Arrangement of slow axis of A-plate and absorption axis of polarizer | Positive C-plate |
|---|---|---|---|
| Polarizing plate 1 | A-1 | 45° | C-1 |
| Polarizing plate 2 | A-2 | 45° | C-1 |
| Polarizing plate 3 | A-3 | 45° | C-1 |
| Polarizing plate 4 | A-1 | Orthogonal | C-1 |
| Polarizing plate 5 | A-2 | Orthogonal | C-1 |
| Polarizing plate 6 | A-3 | Orthogonal | C-1 |

<Mounting in Organic EL Display Device>

GALAXY S IV manufactured by SAMSUNG, having an organic EL display panel installed therein, was disassembled, a circularly polarizing plate was peeled off, and the polarizing plates 1 to 3 manufactured above were each stuck onto the organic EL display panel to manufacture an organic EL display device.

(Reflection)

With regard to the manufactured organic EL display device, a reflection was measured in a specular component excluded (SCE) mode using a colorimeter (CM-2022, manufactured by Konica Minolta, Inc.), the obtained Y values were compared on the basis of the panel before the disassembly, and thus, the manufactured organic EL display device showed a value equal to or lower than that of the panel before the disassembly, and exhibited excellent black display performance with visually suppressed tint inclusion.

<Manufacture of Liquid Crystal Display Device>

A polarizing plate on the visible side was peeled off from a liquid crystal cell of iPad (registered trademark, manufactured by Apple) and used as an IPS-mode liquid crystal cell. Instead of the peeled polarizing plate, the polarizing plates 4 to 6 manufactured above were each stuck onto the liquid crystal cell to manufacture a liquid crystal display device. At this time, the sticking was performed such that the absorption axis of the polarizing plate and the optical axis of the liquid crystal layer in the liquid crystal cell were in directions perpendicular to each other, as observed from a direction perpendicular to the substrate surface of the liquid crystal cell.

The obtained liquid crystal display device was excellent in the front contrast ratio and the tint in an oblique view direction at the time of black display.

<Test on Light Resistance of Positive A-Plate>

The obtained positive A-plates A-1 and A-5 were each transferred to a glass plate using a pressure-sensitive adhesive and a support was peeled off and removed. The obtained laminate was set in a Xenon irradiator (SX75 manufactured by Suga Test Instruments Co., Ltd.) such that the positive A-plate faced a light source side, and the sample was kept at a distance of 290 mm from the light source and irradiated for 2 hours under a condition of 150 W/m$^2$ using a #275 filter. With regard to the laminates before and after the irradiation, each of absorbance changes AAbs in the absorption maximum wavelength belonging to the liquid crystal compound having reciprocal wavelength dispersion was measured using a spectrophotometer (product name "UV-3150", manufactured by Shimadzu Corporation). It could be seen that in a case where AAbs of the positive A-plate A-1 was taken as 1, AAbs of the positive A-plate A-5 was 0.9 or less and the positive A-plate A-5 had particularly remarkable light resistance.

EXPLANATION OF REFERENCES

10: optical film
12: optically anisotropic film
14: alignment film
16: support
18: hard coat layer

What is claimed is:

1. A polymerizable liquid crystal compound represented by Formula (1),
wherein a Clog P value of a group represented by Ar in Formula (1) is 4.3 or more and less than 7.0,

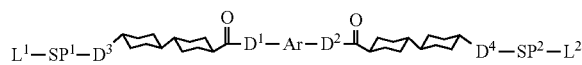

(1)

in Formula (1), $D^1$ and $D^2$ each independently represent —O—, —S—, or —NR$^1$—, $D^3$ and $D^4$ each independently represent a single bond, —O—CO—, —C(=S)O—, —CR$^1$R$^2$—, —CR$^1$R$^2$—CR$^3$R$^4$—, —O—CR$^1$R$^2$—, —CR$^1$R$^2$—O—CR$^3$R$^4$—, —CO—O—CR$^1$R$^2$—, —O—CO—CR$^1$R$^2$—, —CR$^1$R$^2$—O—CO—CR$^3$R$^4$—, —CR$^1$R$^2$—CO—O—CR$^3$R$^4$—, —NR$^1$—CR$^2$R$^3$—, or —CO—NR$^1$—, and R$^1$, R$^2$, R$^3$, and R⁴ each independently represent a hydrogen atom, a fluorine atom, or an alkyl group having 1 to 4 carbon atoms, SP¹ and SP² each independently represent a single bond, a linear or branched alkylene group having 1 to 12 carbon atoms, a branched alkylene group having 3 to 12 carbon atoms, or a divalent linking group in which one or more of —CH₂-'s constituting the linear or branched alkylene group are substituted with —O—, —S—, —NH—, —N(Q)-, or —CO—, and Q represents a substituent, L¹ and L² each independently represent an alkyl group, an aryl group, or a heteroaryl group, each of which may have a substituent, and at least one of L¹ or L² represents a polymerizable group, and Ar is an aromatic ring consisting of the group represented by Formula (Ar-2),

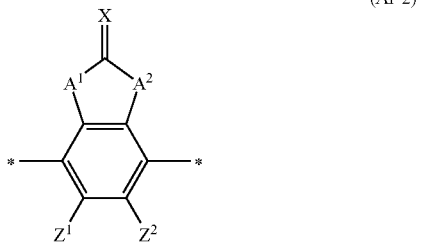

(Ar-2)

in Formulae (Ar-2), * represents a bonding position to D¹ or D²,

Z¹ represents a monovalent aliphatic hydrocarbon group having 3 to 20 carbon atoms, a monovalent aromatic hydrocarbon group having 6 to 20 carbon atoms, a halogen atom, —OR⁶, —NR⁷R⁸, or —SR⁹, Z² represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —OR⁶, —NR⁷R⁸, or —SR⁹, R⁶ to R⁹ each independently represent a hydrogen atom or an alkyl group having 1 to 6 carbon atoms, and Z¹ and Z² may be bonded to each other to form an aromatic ring, A¹ and A² each independently represent a group selected from the group consisting of —O—, —N(R¹⁰)—, —S—, and —CO—, and R¹⁰ represents a hydrogen atom, X represents a non-metal atom of Groups 14 to 16 to which a hydrogen atom, an alkyl group, an alkoxy group, an alkyl-substituted alkoxy group, a cyclic alkyl group, an aryl group, a cyano group, an amino group, a nitro group, an alkylcarbonyl group, a sulfo group, or a hydroxyl group may be bonded.

2. A polymerizable liquid crystal compound represented by Formula (1),
wherein a Clog P value of a group represented by Ar in Formula (1) is 4.3 or more and less than 7.0,

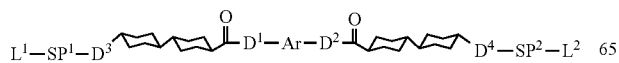

(1)

in Formula (1), D¹ and D² each independently represent —O—, —S—, or —NR¹—, D³ and D⁴ each independently represent a single bond, —O—CO—, —C(=S)O—, —CR¹R²—, —CR¹R²—CR³R⁴—, —O—CR¹R²—, —CR¹R²—O—CR³R⁴—, —CO—O—CR¹R²—, —O—CO—CR¹R²—, —CR¹R²—O—CO—CR³R⁴—, —CR¹R²—CO—O—CR³R⁴—, —NR¹—CR²R³—, or —CO—NR¹—, and R¹, R², R³, and R⁴ each independently represent a hydrogen atom, a fluorine atom, or an alkyl group having 1 to 4 carbon atoms, SP¹ and SP² each independently represent a single bond, a linear alkylene group having 1 to 12 carbon atoms, a branched alkylene group having 3 to 12 carbon atoms, or a divalent linking group in which one or more of —CH₂—'s constituting the linear or branched alkylene group are substituted with —O—, —S—, —NH—, —N(Q)-, or —CO—, and Q represents a substituent, L¹ and L² each independently represent an alkyl group, an aryl group, or a heteroaryl group, each of which may have a substituent, and at least one of L¹ or L² represents a polymerizable group, and Ar is any aromatic ring selected from the group consisting of groups represented by Formulae (Ar-1), (Ar-4), and (Ar-5),

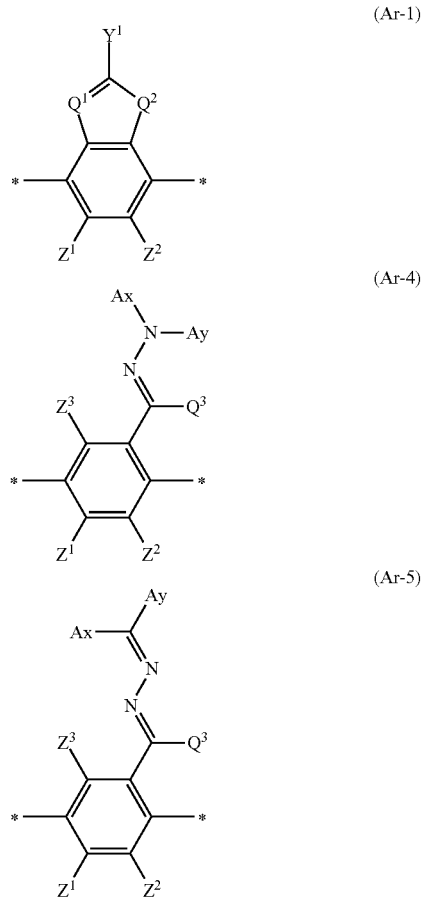

in Formulae (Ar-1), (Ar-4), and (Ar-5), * represents a bonding position to D¹ or D², Q¹ represents N or CH, Q² represents —S—, —O—, or —N(R⁵)—, and R⁵ represents a hydrogen atom or an alkyl group having 1 to 6 carbon atoms, Y$^1$ represents an aromatic hydrocarbon group having 6 to 12 carbon atoms or an aromatic heterocyclic group having 3 to 12 carbon atoms, each of which may have a substituent, Z$^1$ and Z$^2$ each represent a hydrogen atom, Z$^3$ represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —OR$^6$, —NR$^7$R$^8$, or —SR$^9$, R$^6$ to R$^9$ each independently represent a hydrogen atom or an alkyl group having 1 to 6 carbon atoms, and Z$^1$ and Z$^2$ may be bonded to each other to form an aromatic ring, Ax represents an organic group having 2 to 30 carbon atoms, which has at least one aromatic ring selected from the group consisting of an aromatic hydrocarbon ring and an aromatic heterocyclic ring, Ay represents a hydrogen atom, an alkyl group having 1 to 12 carbon atoms, which may have a substituent, or an organic group having 2 to 30 carbon atoms, which has at least one aromatic ring selected from the group consisting of an aromatic hydrocarbon ring and an aromatic heterocyclic ring, the aromatic rings in each of Ax and Ay may have a substituent, and Ax and Ay may be bonded to each other to form a ring, and Q$^3$ represents a hydrogen atom or an alkyl group having 1 to 6 carbon atoms, which may have a substituent.

3. The polymerizable liquid crystal compound according to claim 1,
wherein D$^1$ and D$^2$ in Formula (1) each represent —O—, and D$^3$ and D$^4$ in Formula (1) each represent —O—CO—.

4. The polymerizable liquid crystal compound according to claim 2,
wherein D$^1$ and D$^2$ in Formula (1) each represent —O—, and D$^3$ and D$^4$ in Formula (1) each represent —O—CO—.

5. A polymerizable liquid crystal composition comprising: the polymerizable liquid crystal compound according to claim 1.

6. A polymerizable liquid crystal composition comprising: the polymerizable liquid crystal compound according to claim 2.

7. A polymerizable liquid crystal composition comprising: the polymerizable liquid crystal compound according to claim 2.

8. A polymerizable liquid crystal composition comprising: the polymerizable liquid crystal compound according to claim 4.

9. The polymerizable liquid crystal composition according to claim 6, further comprising:
a polymerizable compound having one or more polymerizable groups, which is different from the polymerizable liquid crystal compound.

10. An optically anisotropic film obtained by polymerization of the polymerizable liquid crystal composition according to claim 6.

11. An optically anisotropic film obtained by polymerization of the polymerizable liquid crystal composition according to claim 9.

12. An optical film comprising the optically anisotropic film according to claim 10.

13. An optical film comprising the optically anisotropic film according to claim 11.

14. A polarizing plate comprising:
the optical film according to claim 12; and
a polarizer.

15. An image display device comprising:
the optical film according to claim 12.

16. An image display device comprising:
the polarizing plate according to claim 14.

* * * * *